United States Patent
Burnette, III

(12) 
(10) Patent No.: US 7,144,576 B1
(45) Date of Patent: Dec. 5, 2006

(54) **MODIFIED *PERTUSSIS* TOXIN**

(75) Inventor: Walter Neal Burnette, III, Thousand Oaks, CA (US)

(73) Assignee: Amgen, Inc., Thousand Oaks, CA (US)

( * ) Notice: Subject to any disclaimer, the term of this patent is extended or adjusted under 35 U.S.C. 154(b) by 0 days.

(21) Appl. No.: 08/448,727

(22) Filed: May 24, 1995

Related U.S. Application Data

(60) Division of application No. 08/034,460, filed on Mar. 18, 1993, now abandoned, which is a continuation of application No. 07/232,482, filed on Aug. 17, 1988, now abandoned, which is a continuation-in-part of application No. 07/094,307, filed on Sep. 4, 1987, now abandoned.

(51) Int. Cl.
*A61K 39/10* (2006.01)

(52) U.S. Cl. .................. 424/190.1; 424/240.1

(58) Field of Classification Search ............ 424/236.1, 424/253.1, 254.1, 832; 530/350; 435/69.1, 435/69.3
See application file for complete search history.

(56) References Cited

U.S. PATENT DOCUMENTS 4,883,761 A * 11/1989 Keith et al. ................. 435/320

OTHER PUBLICATIONS

Pizza et al Science 246:497-500 1989.*
Black Ann Sclavo No. 1-2 pp. 175-182 1986.*
Burnette et al Science 242:72-74, 1988.*
Maniatis et al. Molecular Cloning A Laboratory Manual, Cold Spring Harbor Laboratory, New York pp. 403-433 (1982).*
Nicosia et al., *Infection and Immunity*, vol. 55, No. 4, pp. 963-967 (1987).
Nicosia et al., *Proc. Natl. Acad. Sci. USA*, vol. 83, pp. 4631-4635 (1986).
Zuxker et al., *Molecular Immunology*, vol. 21, No. 9, pp. 785-792 (1984).
Shortle et al., *Annual Review of Genetics*, vol. 15, pp. 265-292 (1981).
Chen et al., *J. Bacteriol.*, vol. 161, pp. 758-763 (1985).
Locht et al., *Science*, vol. 232, pp. 1258-1264 (1986).

* cited by examiner

*Primary Examiner*—John S. Brusca
(74) *Attorney, Agent, or Firm*—Perkins Coie LLP

(57) ABSTRACT

The development of subunits and subunit analogs of the *Bordetella* exotoxin by recombinant DNA techniques provides vaccine products that retain their biological activity, are highly immunogenic, and can confer protection against disease challenge. Genetically-engineered modifications of the subunits can result in products that retain immunogenicity, yet are free of enzymatic activity associated with toxin of reactogenicity.

18 Claims, 13 Drawing Sheets

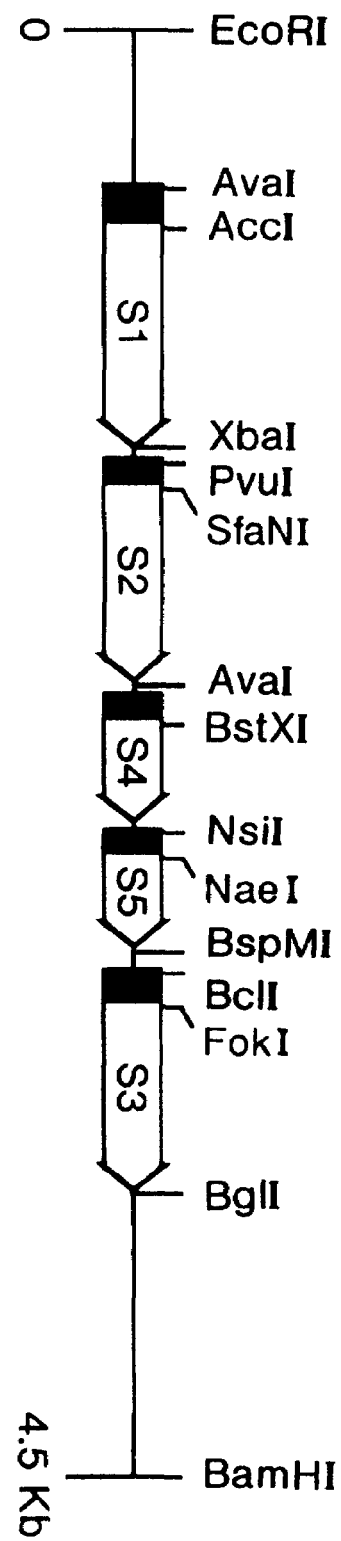
FIG. I
*PRIOR ART*

DIRECTLY-EXPRESSED PTX SUBUNITS

METHIONYL PTX SUBUNITS

FIG. 7
PRIOR ART

```
1                   10                  20
MetValProProAlaThrValTyrLysTyrAspSerArgProProGluAspValPheGln 21                  30                  40
AsnGlyPheThrAlaTrpGlyAsnAsnAspAsnValLeuAspHisLeuThrGlyArgSer 41                  50                  60
CysGlnValGlySerSerAsnSerAlaPheValSerThrSerSerArgArgTyrThr 61                  70                  80
GluValTyrLeuGluHisArgMetGlnGluAlaValGluAlaGluArgAlaGlyArgGly 81                  90                  100
ThrGlyHisPheIleGlyTyrIleTyrGluValArgAlaAspAsnAsnPheTyrGlyAla 101                 110                 120
AlaSerSerTyrPheGluTyrValAspThrTyrGlyAspAsnAlaGlyArgIleLeuAla 121                 130                 140
GlyAlaLeuAlaThrTyrGlnSerGluTyrLeuAlaHisArgArgIleProProGluAsn 141                 150                 160
IleArgArgValThrArgValTyrHisAsnGlyIleThrGlyGluThrThrThrThrGlu 161                 170                 180
TyrSerAsnAlaArgTyrValSerGlnGlnThrArgAlaAsnProAsnProTyrThrSer 181                 190                 200
ArgArgSerValAlaSerIleValGlyThrLeuValArgMetAlaProValIleGlyAla 201                 210                 220
CysMetAlaArgGlnAlaGluSerSerGluAlaMetAlaAlaTrpSerGluArgAlaGly 221                 230         235
GluAlaMetValLeuValTyrTyrGluSerIleAlaTyrSerPhe
```

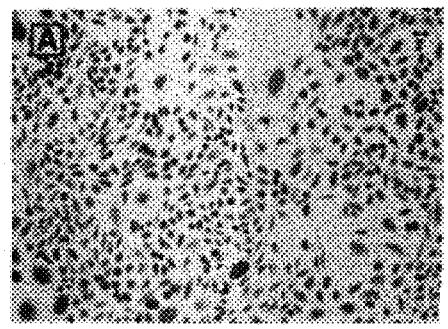
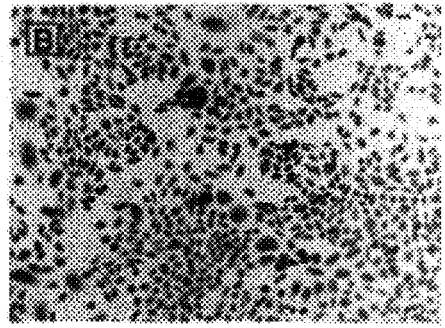
FIG. 11A  FIG. 11B
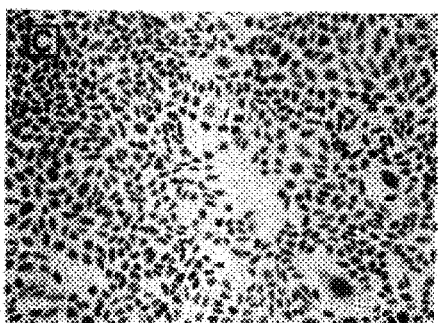
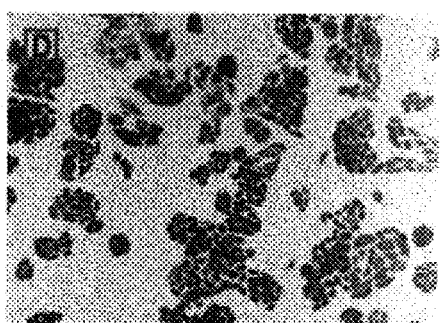
FIG. 11C  FIG. 11D
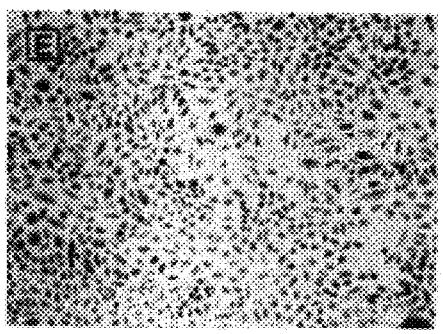
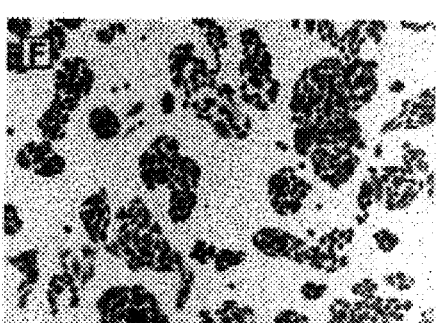
FIG. 11E  FIG. 11F

MODIFIED *PERTUSSIS* TOXIN

This application is a divisional application of prior application Ser. No. 08/034,460, filed Mar. 18, 1993 Now ABN., which in turn is a continuation application of prior application Ser. No. 07/232,482, filed Aug. 17, 1988, now abandoned, which in turn is a continuation-in-part application of prior application Ser. No. 07/094,307, filed Sep. 4, 1987, now abandoned.

BACKGROUND OF THE INVENTION

The present invention provides high-level, direct recombinant expression of subunit analogs of S1, S2, S3, S4, and S5 of *Bordetella* exotoxin in *E. coli* without resort to fusions with portions of heterologous proteins. More particularly, genetically-engineered modifications of the subunits provide a class of *Bordetella* toxin analogs having the capability to elicit toxin-neutralizing levels of antibodies, and to be substantially free of reactogenic components. Genetically-engineered subunits can be used to produce subunit vaccine(s) which have immunogenic efficacy and are substantially free of reactogenic components.

The term *Bordetella* exotoxin denotes a group of toxins encoded by the genomes of various species of *Bordetella*, such as *B. pertussis, B. parapertussis* and *B. bronchiseptica*. Other terms commonly used to designate *Bordetella* exotoxin are pertussis toxin ("PTX"), lymphocytosis-promoting factor ("LPF"), and islet-activating protein ("IAP").

Whooping cough remains a major cause of infant morbidity and mortality in many parts of the world. Whole-cell *Bordetella pertussis* vaccines have provided an effective means for controlling this disease. However, the use of such vaccines has been directly correlated with mild side effects and temporally related to more severe, and occasionally fatal, neurological events.

Extensive efforts have been expended in an effort to eliminate the harmful side-effects known to be associated with the current vaccines. These have resulted in the production and testing of acellular vaccines, and in basic research in an effort to develop safer recombinant products. A critical first step toward cloning and developing a recombinant DNA-derived vaccine was sequencing of the pertussis toxin operon and subsequent deduction of the amino acid sequences of the individual subunits. (Locht, C. and Keith, J. M., 1986, Science 232: 1258–1264; Locht et al., 1986, Nucl. Acids Res. 14: 3251–3261; and Nicosia et al., 1986, Proc. Natl. Acad. Sci. USA 83: 4631–4635).

Nicosia et al. (1987, Infect. Immun., 55: 963–967) demonstrated that mRNA encoding each of subunits S1, S2, S3, S4, and S5 of *Bordetella pertussis* could be efficiently transcribed from the cloned genes in *E. coli*. Although they purported to show high levels of transcription of the native pertussis toxin polycistronic message, the amount of proteins produced by direct expression was very low or undetectable. Further, fusion proteins which were subsequently synthesized were incapable of eliciting any neutralizing or protective immune responses.

Barbieri et al. (1987, Infect. Immun., 55: 1321–1323) demonstrated the expression of the S1 subunit as a fusion protein in *E. coli*. This fusion protein contains the first six amino acids of beta-galactosidase, five amino acids encoded by the pUC18 polylinker, followed by amino acids 2 through 235 of the S1 subunit. The S1 fusion protein, produced in low amounts, had only about 25% of ADP-ribosyltranferase activity of authentic or native pertussis toxin.

Locht et al. (Abstract, Modern Approaches to New Vaccines, Cold Spring Harbor Laboratory, Cold Spring Harbor, N.Y., Sep. 9–14, 1986) were able to express a fusion protein containing amino acids 2 through 187 of the S1 subunit. They predicted that the construct would not have toxic activity because they believed it lacked the NAD-binding site associated with the ADP-ribosyltranferase, the enzymatic activity believed to be responsible for the reactogenicity of the toxin. Subsequent experiments with this molecule indicated that this truncated species possessed essentially undiminished enzymatic activity. None of the known prior art subunits or subunit analogs have the capability of eliciting toxin-neutralizing levels of antibodies and are substantially free of enzymatic activity associated with reactogenicity.

BRIEF DESCRIPTION OF THE FIGURES

FIG. 1 is a schematic representation of the cistron order of the PTX operon (Prior art Locht and Keith, supra). The regions marked S1, S2, S4, S5, and S3 indicate the proposed open reading frames for each these PTX subunits. The filled area just prior to each cistron denotes the putative signal sequence. The restriction enzyme site immediately downstream of each cistronic element indicates the downstream restriction site used in the subcloning of that cistron into the expression vector. The restriction enzyme site located just inside each signal sequence region was utilized as the upstream restriction site for the subcloning of the full-length cistron into the expression vector with an appropriate oligodeoxynucleotide linker to produce the immature PTX subunit with its signal sequence intact. The restriction enzyme site just inside the each mature PTX subunit open reading frame was used, with an appropriate oligodeoxynucleotide linker, as the upstream restriction site for the subcloning of the cistron without its encoded signal sequence to produce a methionyl-mature PTX subunit.

FIG. 2B shows the products of expression as methionyl-mature recombinant (rm) subunits. These subunits are made in significant quantities with the exception of rmS1 (not shown).

FIG. 7 is the deduced amino acid sequence of rS1 mutant deriving from expression of pTXS1 (6A-3/4-1) (SEQ ID NO: 27).

FIGS. 11A–J is a photograph of cell monolayers examined for the presence of cell clusters by light microscopy.

SUMMARY OF THE INVENTION

The present invention provides a recombinant DNA molecule comprising at least a portion encoding subunit S1 of Bordetella exotoxin, or a fragment or derivative of said portion wherein said portion or fragment or derivative encodes a polypeptide having a biological activity which can (a) elicit toxin-neutralizing levels of antibodies and (b) is substantially free of reactogenic components. The polypeptide S1 subunit, or subunit analogs thereof, comprises a major epitope known to be important in providing immunoprotection against pertussis toxicity. The toxin-neutralizing levels of antibodies provide immunoprotection against pertussis toxicity. Site-specific mutagenesis results in an analog of subunit S1 which is substantially inactive enzymatically.

The genetically engineered S1 subunit of Bordetella exotoxin, and the analogs of this subunit, provide recombinant DNA-derived subunit vaccine materials for use in the prevention of pertussis disease. The S1 subunit and its analogs can provide vaccine products, either alone or in combination with subunits S2, S3, S4, and S5, and mixtures thereof. Subunits S2, S3, S4, and S5 can be purified from B. pertussis or be recombinantly derived as fusion or non-fusion products. High levels of recombinant expression of subunits S2, S3, S4 and S5 of Bordetella exotoxin have also been achieved in E. coli by direct non-fusion methods. Alternative recombinant hosts, including yeast for example S. cerivisiae, and bacterial organisms, for example, Salmonella typhimurium or typhi, Bacillus, sp., and viruses, for example vaccinia, may be used for expression of these subunit analogs.

DETAILED DESCRIPTION

The present invention provides high-level, direct recombinant expression of all PTX subunits necessary for vaccine production. Further, S1 subunit analogs provide biological activity that is highly immunogenic and substantially free of reactogenic components, such components being enzymatic activities of the toxin molecule related to its toxicity and reactogenicity and extraneous components of B. pertussis (e.g. endotoxin) which would be found with vaccine materials extracted from B. pertussis cells and are known to be reactogenic. The S1 analogs used alone, or in combination with other subunits of PTX, can provide vaccine products that are efficacious and greatly reduce the liklihood of side-effects from reactogenic components existing in non-modified native or recombinant-derived subunits.

Figure 2A:
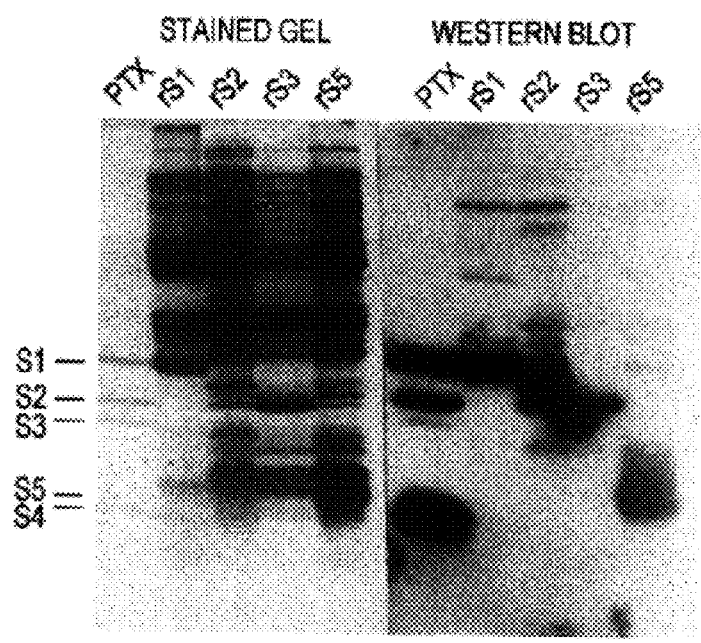
FIGS. 2A and 2B are an SDS-polyacrylamide gel and Western blot of recombinant PTX subunits. The left-hand side of FIG. 2A shows a Coomassie Brilliant Blue-stained gel of the recombinant PTX subunits produced in measurable amounts; the right-hand side of FIG. 2A is a Western blot of a parallel gel utilizing a rabbit polyclonal anti-PTX hyperimmune serum. PTX indicates the lanes containing commercial-grade pertussis toxin. These results demonstrate that recombinant (r) S1, S2, S3, and S5 were all produced in significant amounts. The Western blot shows that rS1 is fully-processed from its preprotein species, rS2 and rS5 are partially processed, and rS3 is not substantially processed under the conditions of fermentation; rS4 was not produced in sufficient amounts to be visualized.
Figure 2B:
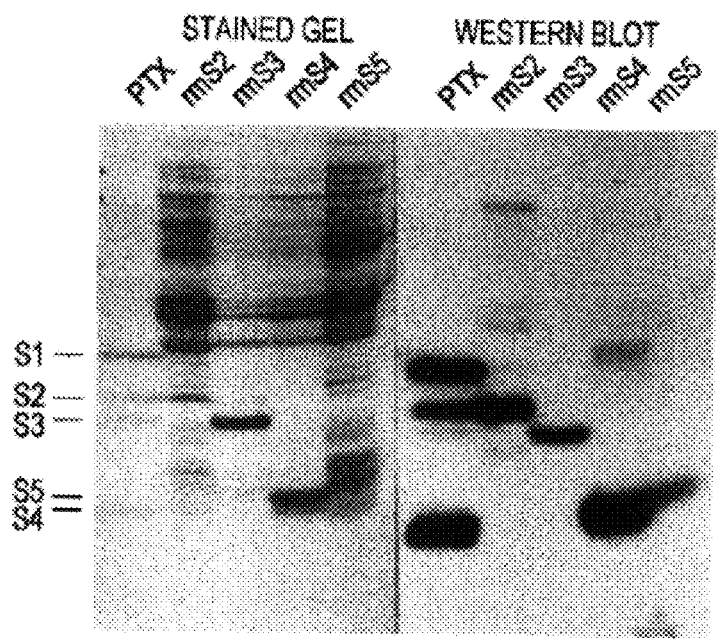

The individual subunits S1, S2, S3, S4, and S5 of Bordetella pertussis toxin were each subcloned and directly expressed individually in E. coli. The signal sequence appears to play an important role in the expression of recombinant S1 (rS1). In the absence of a signal peptide, insignificant amounts of rS1 were expressed in E. coli. If either the native leader of the S1 subunit or a synthetic leader is present on the preprotein, high levels of expression, in the range of 10–30% of total cell protein, are obtained. The fermentation of rS1 expressor cells at the production scale in a fed-batch 10-liter fermentor (at a non-optimized expression level of 8 mg S1/OD-L) resulted in nearly complete proteolytic processing of rS1 to its mature species, as shown in FIG. 2. Fermentation of expresser cells on a laboratory scale gave rise to incompletely processed S1; both preprotein and mature protein were found following logarithmic cell growth. The failure of a synthetic E. coli cleavable leader sequence to enhance signal processing suggested that incomplete cleavage is not the result of incompatible recognition of E. coli leader peptidases for B. pertussis proteolytic cleavage sites. The failure to overcome the processing block, either by increasing signal peptidase synthesis using cells co-transformed with a plasmid expressing E. coli leader peptidase at high levels or by reducing S1 expression levels with the use of a low-copy-number vector, indicated that the problem does not lie in saturation of the cleavage pathway. These results demonstrate that post-translational processing of foreign proteins in E. coli may be controlled by poorly-understood mechanisms related to the physiological state of the growing cell.

PTX subunits S2, S3, S4, and S5 were similarly expressed in E. coli. as shown in FIG. 2. Like recombinant S1, the rS2, rS3, and rS5 subunits appeared to exhibit incomplete processing at laboratory-scale fermentation. Because rS1 could be fully processed at the production scale, similiar fermentation conditions can be utilized to yield the other subunits in completely processed forms. In contradistinction to rS1, the rS4 subunit could be expressed at high levels as a mature methionyl polypeptide, but was not detectable when expressed with its natural leader peptide sequence. Subunits S2, S3, S4, and S5 have now all been expressed as methionyl mature polypeptides. Amino acid analysis of these molecules demonstrates that the heterologous (non-native) methionyl residue is substantially removed from each species (with the exception of S4) by cellular methione aminopeptidase to provide fully mature proteins of native sequence. The methionyl residue is not substantially removed from recombinant S4 because of the incompatibility of the amino terminal recognition sequence for the cellular enzyme. All the recombinant proteins were recovered as inclusion bodies from lysed cells. The subunits were found to have migration patterns in SDS-PAGE essentially identical to authentic native subunits or to react in Western blots with monoclonal and polyclonal antitoxin sera. As shown in FIG. 2, high-level recombinant expression of subunits S1, S2, S3, S4 and S5 subunits in E. coli are achieved by direct, non-fusion means.

Although alternative methods and materials could be used in the practice of the present invention, the preferred methods and materials are described below. All references cited hereunder are incorporated herein by reference.

Materials and Methods for Recombinant Expression of Subunits S1, S2, S3, S4 and S5

Materials. DNA modifying enzymes were purchased from New England Biolabs, (Beverly, Mass.), Bethesda Research Laboratories, (Gaithersburg, Md.), Boehringer Mannheim Biochemicals, (Indianapolis, Ind.), and International Biotechnologies, Inc., (New Haven, Conn.); enzymes were used according to manufacturers recommendations. All chemicals and biochemicals were analytical reagent grade. Purified pertussis toxin PTX was purchased from List Biological Laboratories, Inc. (Campbell, Calif.). Synthetic oligonucleotides were synthesized according to Caruthers (1982, in H. G. Gussen and A. Lang [eds] Chemical and enzymatic synthesis of gene fragments, Verlag Chemie, Weinheim, FRG, pp 71–79.). Rabbit antisera against whole PTX were produced at Antibodies, Inc. (Davis, Calif.) and the NIAID Rocky Mountain Laboratory Mmonoclonal antibodies against subunits from native PTX were produced by standard methods (Kohler and Milstein, 1975, Nature 256: 495–497; Nowinski et al., 1979, Virology 93:111–126). Radioiodinated protein A and rabbit anti-mouse IgG were purchased from New England Nuclear (Wilmington, Del.). Anti-S1 monoclonal antibody IB7 (as described in Sato et al., 1987, Infect. Immun. 55:909–915,) was a gift of H. Sato, NIH, to Keyo, Japan.

Plasmids and bacterial strains. Plasmid pPTX42 containing the PTX operon has been described (see Locht and Keith, supra and Locht et al., supra). Expression plasmids pCFM1036, pCFM1146, pCFM1152, and pCFM1156 were derived at Amgen.

A detailed description of Amgen's expression vector system is described in published European Patent Application No. 136,490 and incorporated herein by reference. Such plasmids may contain an inducible promoter, a synthetic ribosome binding site, a cloning cluster, plasmid origin of replication, a transcription terminator, genes regulating plasmid copy number, and a Kanamycin resistance gene. The derived plasmids differ from each other in a number of respects. The plasmid pCFM1036 can be derived from pCFM836 (European Patent Application No.) 136,490 by substituting the DNA sequence between the unique AatII and EcoRI restriction sites containing the synthetic $P_L$ promoter with the following oligonucleotides:

```
         AatII                 EcoRI
    5' CATCGATTCTAG 3' (SEQ ID NO:1)

3' TGCAGTAGCTAAGATCTTAA (SEQ ID NO:2)
```

The plasmid contains no inducible promoter preceding the restriction cluster. The plasmid pCFM1146 can be derived from pCFM836 by substituting the small DNA sequence between the unique ClaI and XbaI restriction sites with the following oligonucleotide:

```
        ClaI                       XbaI
   5'   CGATTTGATT    3' (SEQ ID NO:3)

3'         TAAACTAAGATC 5' (SEQ ID NO:4)
``` and by destroying the two endogenous NdeI restriction sites by end filling with T4 polymerase enzyme followed by blunt end ligation. The plasmid contains no synthetic ribosome binding site immediately preceding the restriction cluster. The plasmid pCFM1156 can be derived from pCFM1146 by substitution of the small DNA sequence between the unique XbaI and KpnI restriction sites with the following oligonucleotide:

```
       XbaI                                                  KpnI
  5' CTAGAAGGAAGGAATAACATATGGTTAACGCGTTGGAATTCGGTAC 3' (SEQ ID NO:5)

3'     TTCCTTCCTTATTGTATACCAATTGCGCAACCTTAAGC 5' (SEQ ID NO:6)
```

The plasmid pCFM1152 can be derived from pCFM1156 by substituting the BglII to BglII (248 base pair) DNA fragment constituting the copB promoter and encoding a portion of the copB gene with the corresponding DNA fragment from the plasmid pCFM512 (European patent application No. 136,490). This plasmid has a lower copy number than pCFM1156.

Plasmids pBR322, pUC18, pUC19, and phage M13mp18 and M13mp19 DNA were purchased from Bethesda Research Laboratories. The plasmid pTD125 containing the gene for E. coli leader peptidase (Dale, T. 1983, J. Bacteriol. 143:76–83) was a gift of W. Wickner (UCLA). E. coli FM5 cells were derived at Amgen Inc., Thousand Oaks, Calif. from E. coli K-12 strain from C.F. Morris (Bachmann et. al., 1976, Bacteriol. Rev. 40: 116–167) and contain the integrated lambda phage repressor gene, $CI_{857}$ (Sussman, et al., 1962, C.R. Acad. Sci. 254:1517–1579). Construction of the individual subunit expression plasmids is described herein. Vector production, cell transformation, and colony selection were performed by standard methods (Maniatis et al., 1982, Molecular cloning: a laboratory manual. Cold Springs Harbor Laboratory, NY).

Analytical procedures. DNA sequencing was done by the primer-extension, chain-termination method (Sanger et al., 1977. Proc. Natl. Acad. Sci. USA 74: 5463–5467; Heidecker et al., 1980, Gene 10:69–73). Protein sequence analyses were performed by automated Edman degradation in an ABI 470A gas-phase microsequenator (Hewick et al., 1981, J. Biol. Chem. 256:7990–7997; Hunkapillar et al., 1983. Meth. Enzymol. 91:399–413.). SDS-polyacrylamide gel electrophoresis (.SDS-PAGE) was performed as described by Laemmli (1970, Nature 227:680–685), elution of polypeptides from polyacrylamide gels was by the method of Hunkapiller et al. (1983, Meth. Enzymol. 91:227–236), and Western blotting was performed as described by Burnette (1981, Analyt Biochem. 112:195–203). The ratio of recombinant protein to total cellular protein or total inclusion-body protein was assessed by SDS-PAGE of whole-cell lysates or inclusion-body preparations followed by staining with Coomassie Brilliant Blue R250 and subsequent gel scanning by integrative densitometry. Assays for NAD-glycohydrolase and ADP-ribosyltransferase were done as described previously (Katada et al. 1982, Proc. Natl. Acad. Sci. USA 79:

3129–3133; Lim et al. 1985, J. Biol. Chem. 260: 2585–2588). Reduction in the morphological response of CHO cells to PTX (Hewlett et al. 1983, Infect. Immun. 40:1198–1203) with antisera against various recombinant subunit preparations was performed by the procedure of Gillenius et al. (1985, J. Biol. Stand. 13:61–66).

Construction of expression plasmids. All plasmids were constructed from a series of *E. coli* generalized expression vectors differing as described previously. The individual pertussis toxin subunit gene segments were isolated using the restriction sites shown in prior art FIG. 1; the upstream restriction site was just inside the initiation codon for expression of the signal peptide-containing form of the subunit or just inside the codon for the amino-terminal residue of the mature, processed form of the subunit for expression of the methionyl-mature form of the subunit analog. Co-expression of the entire B oligomer utilized, in one case, the fragment containing the upstream non-coding region of S2 through the end of S3 and omitted the synthetic ribosome binding site of the *E. coli* expression vector; in the other case, the upstream non-coding region of S2 was deleted and the synthetic *E. coli* ribosome binding site was inserted. Synthetic oligonucleotide linkers were employed to effect insertion of the gene segments into the expression plasmids at an optimal distance downstream of the synthetic promoter and ribosome binding site. The upstream linkers restored the reading frame of each gene either back to the authentic initiation codon, in the case of pre-subunit constructions, or to the first codon of the mature amino terminus; the latter oligonucleotides included a methionyl initiation codon. In some cases, codon usage was modified to reduce the potential for secondary structure near the 5' end of the resultant mRNAs. For example, the cysteine codon at position 3 in the signal region of the S1 subunit (Locht and Keith supra,) was substituted with the codon for serine to eliminate the possibility of detrimental disulfide interactions.

Following transformation of *E. coli* FM5 cells with the various plasmid constructs and plating on Kanamycin-containing agar, appropriate numbers of colonies were selected, replica-plated, grown as small liquid cultures (“minipreps”), and induced at 42° C. for 4 h. The minipreps were then screened by light microscopy for the presence of inclusion bodies in the bacterial cells. Preparations exhibiting apparent inclusions were identified and matching colonies from the replica plates subjected to flask-scale (one liter) laboratory fermentation at the induction temperature; some preparations were later subjected to fed-batch fermentation in 10-liter industrial fermentors. Samples were removed from fermentation at various times post-induction and examined for the appearance of the appropriate PTX subunit by SDS-PAGE followed by both Coomassie Brilliant Blue-staining and Western blotting; blots were first reacted with an appropriate monoclonal antibody, examined by autoradiography, and then reacted with a polyclonal anti-PTX serum and followed by further autoradiography. The structure of the plasmid from each expression clone was confirmed by restriction mapping of the isolated plasmid and verified by DNA sequencing of junction regions.

Expression of recombinant S1. When *E. coli* cells containing the S1 expression plasmid (pPTXS1/1) were induced at 42° C. in a fed-batch 10-liter fermentor at the production scale, they produced a major intracellular protein of approximately 26,000 daltons (FIG. 2A left, lane rS1) which comigrated with authentic PTX S1 in SDS-PAGE. Partial amino acid sequence analysis (5 cycles) established that this polypeptide had the amino terminal sequence predicted for the mature S1 subunit (Locht and Keith, supra). The protein was immunochemically identified as S1 by its reactivity with a mouse anti-S1 monoclonal antibody in a Western blot (FIG. 2A right, lane rS1).

It should be noted that laboratory fermentation of the S1 expresser cells at the one-liter flask scale resulted in incomplete cleavage of the rS1 signal peptide, a phenomenon also observed for the expression of the other PTX subunits in *E. coli* (see below). Attempts were made to identify the molecular block to signal processing seen at the flask scale by a series of experiments designed to increase the extent of preprotein cleavage: insertion of the S1 gene into a low-copy-number expression vector, substitution of a synthetic *E. coli* cleavable signal sequence (Picker et al., 1983, Infect. Immun. 42:269–275.) for the authentic S1 signal peptide, and co-transformation of the subunit-expressing cells with an expression plasmid containing the gene for *E. coli* leader peptidase (Date, supra.) to increase the constitutive level of this enzyme. None of these approaches led to any significant alteration in signal cleavage. However, modification of the fermentation conditions to a fed-batch process led to processing of pre-S1 to its mature form that was substantially complete.

The success in expressing the S4 subunit as a mature methionyl polypeptide (below) prompted the employment of the same strategy with rS1. Unlike rS4 expression in *E. coli*, however, the expression of mature methionyl S1 was so low that a Western blot was required for its detection. In contrast, the expression of rS1 using its authentic signal sequence yielded the fully processed polypeptide at levels of 10–30% of the total cell protein. As described later, truncation of the mature amino terminus of rS1 by recombinant means can result in very high levels of expression. In fact, substitution of as little as the first two residues of the mature S1 sequence (AspAsp) with Metval results in significant expression relative to the methionyl mature form.

Expression of S2, S3, S4, and S5. As a test of feasibility, the PTX S4 subunit was first expressed as a mature methionyl protein without its native leader peptide and, as described above, was produced at high levels in *E. coli* (FIG. 2B left, rmS4 lane). Although its migration in SDS-PAGE was slightly retarded relative to that of S4 from whole toxin preparations, it had the predicted S4 amino acid sequence. S4 purified from *B. pertussis* by HPLC exhibits the same retardation in gel electrophoresis (Locht et al. supra). Recombinant S4 reacts well with polyclonal antisera in Western blots (FIG. 2B right, lanrem S4), but has reduced reactivity with an S4 monoclonal antibody.

In contradistinction to the results obtained with S1, expression of S4 with its native leader peptide sequence (Locht and Keith, supra resulted in undetectable levels of protein (not shown). It should be noted, however, that Nicosia et al. (supra) predict a different translational start site further upstream; it is possible that use of this additional sequence in the S4 leader peptide would result in much higher levels of expression. Recombinant S2, S3, and S5 were each expressed with their native leader sequences (FIG. 2A, lanes rS2, rS3, and rS5, respectively); none of these subunits was completely processed during laboratory-scale fermentation, although preliminary production-scale fermentation experiments using the fed-batch process gives marked improvement in the processing of S2 and S5. S2, S3, and S5 were also each expressed in *E. coli* in a methionyl-mature form at levels comparable to those obtained with their native leader peptides (FIG. 2B, lanes rmS2, rmS3, and rmS5, respectively). As noted above, the heterologous methionine residues of S2, S3, and S5 are processed by cellular methione amino-peptidase to yield fully-mature polypeptides of native sequence.

Figure 3:
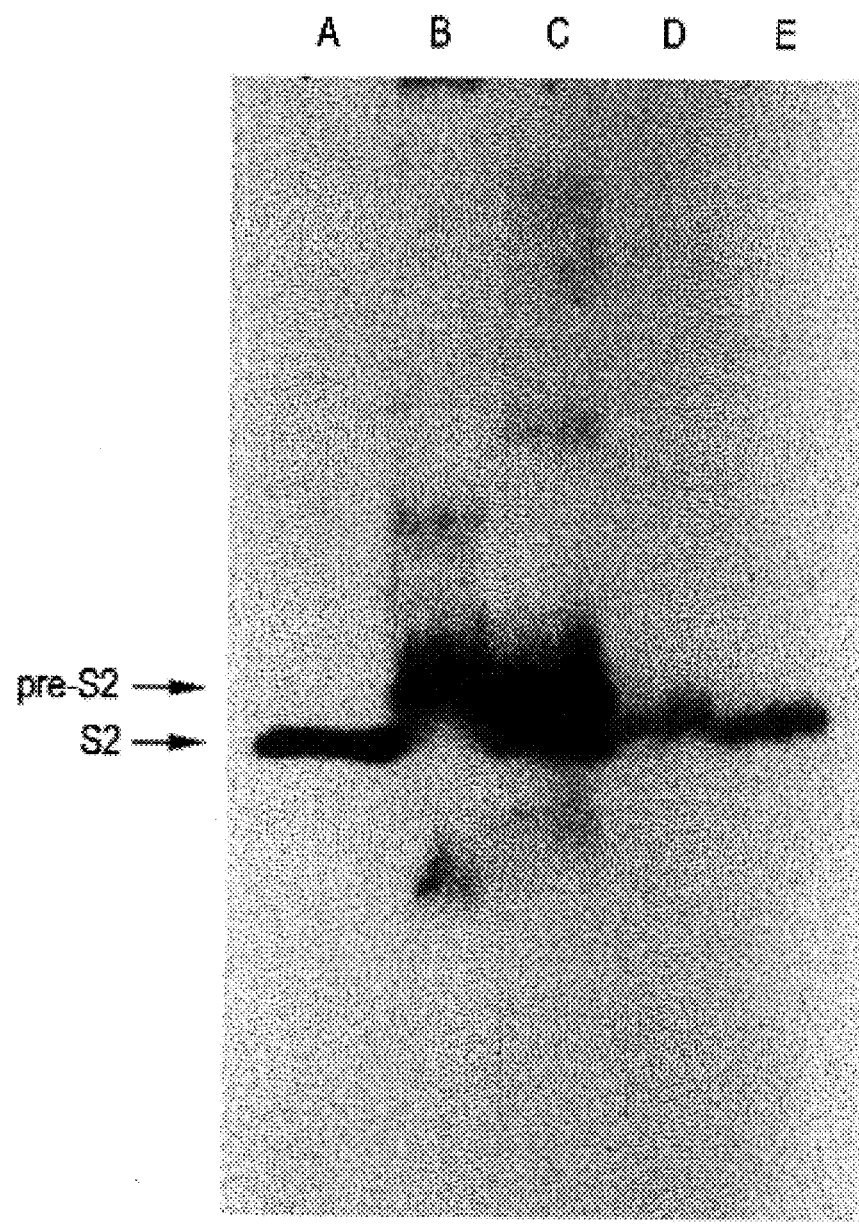
FIG. 3 is a Western blot demonstrating the effect of upstream noncoding sequences on the expression of rS2. The details of the figure are given in the text.

The entire polycistronic segment representing the B oligomer subunits (S2-S4-S5-S3) was expressed under control of the $P_L$ promoter. FIG. 3 illustrates the effects of the upstream non-coding region on production of the S2 subunit. In one case, the expression plasmid retained the entire intercistronic portion between the termination codon of S1 and the initiation codon of S2 (Locht and Keith, supra), but without the synthetic ribosome binding site used in all the other expression plasmids. This resulted in the synthesis of recombinant S2 which appeared to be completely processed when examined in a Western blot with an anti-S2 monoclonal antibody (FIG. 3, lanes D and E); although not shown, polyclonal antibody analysis suggested that the other B oligomer subunits were also fully processed to their mature forms. Substitution of the non-coding intercistronic segment with the synthetic Shine-Delgarno sequence resulted in a much higher level of rS2 synthesis (FIG. 3, lanes B and C); however, this material is incompletely processed. The efficiency of synthesis of each cistron appears to be directly correlated to its proximity with the 5' end of the message, i.e., S2>S4>S5>S3. A preliminary experiment in which the remainder of the operon is placed downstream from the highly-expressing S1 construct (see above) resulted in very low levels of synthesis and incomplete processing of each of the subunits, including S1).

Properties of recombinant PTX subunits. Very little, if any, of the processed PTX subunits appear to be secreted from the E. coli cells, although there is some indication that fully processed rS1 may be found to a limited extent in the periplasmic space. The bulk of each subunit was found in the form of inclusion bodies and constituted 10–30% of total cellular protein. Cell lysis by French press and low-speed centrifugation resulted in pellet fractions that contained up to 65% of their protein as the individual subunits.

All the PTX subunits were detectable in Western blots with a polyclonal rabbit antitoxin serum (FIG. 2). As noted above, subunits rS1 and rS2 reacted well with specific monoclonal antibodies in Western blots. Recombinant S4, made as a methionyl polypeptide, had reduced reactivity with an anti-S4 monoclonal antibody. Monoclonal antibodies against subunits S3 and S5 were not available, although rS3 could be detected on a Western blot with anti-S2 monoclonal antibody by virtue of its close sequence homology with S2 (Locht and Keith, supra).

Figure 4:
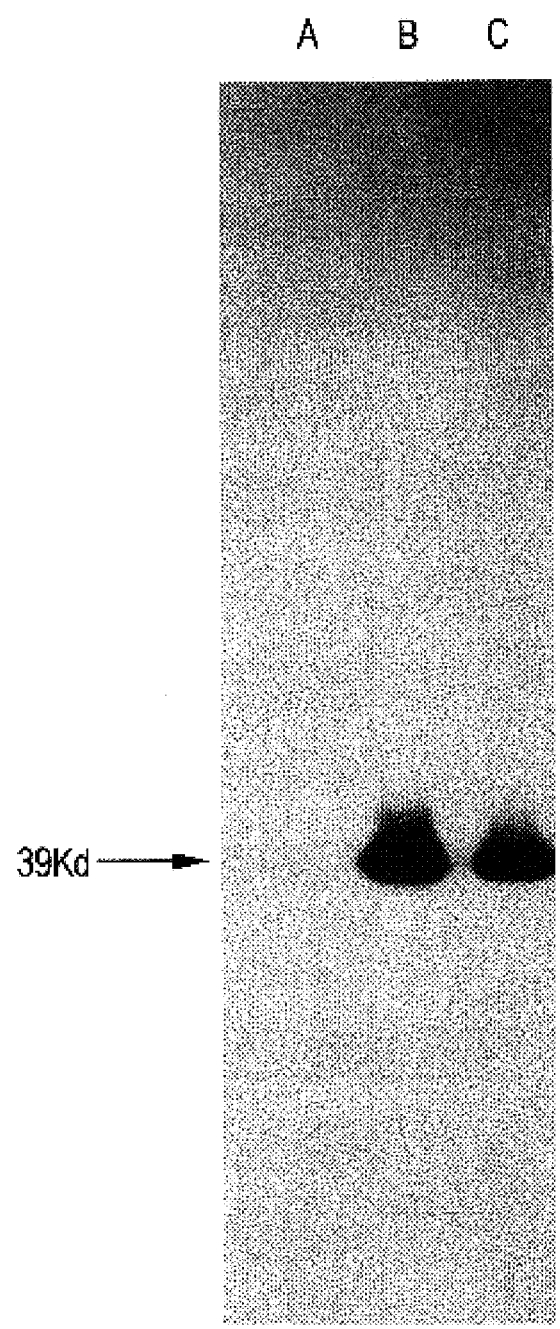
FIG. 4 is an autoradiogram of a SDS-polyacrylamide gel demonstrating ADP-ribosyltransferase activity of recombinant S1. Recombinant S1 (500 ng), purified native pertussis toxin (1 ug), and reaction buffer were individually reacted with bovine transducin in the presence of [$^{32}$P]NAD essentially as described by Manning et al. 1984, J. Biol. Chem. 259:749–756; West et al. 1985, J. Biol. Chem. 260:14428–14430). The samples were precipitated with cold 10% trichloroacetic acid, the precipitates subjected to SDS-PAGE and subsequent autoradiography. The radioactive band at 39 Kd is the transducin subunit which has been ribosylated. Lane A, reaction buffer control; lane B, native PTX; lane C, rS1.
Figure 5:
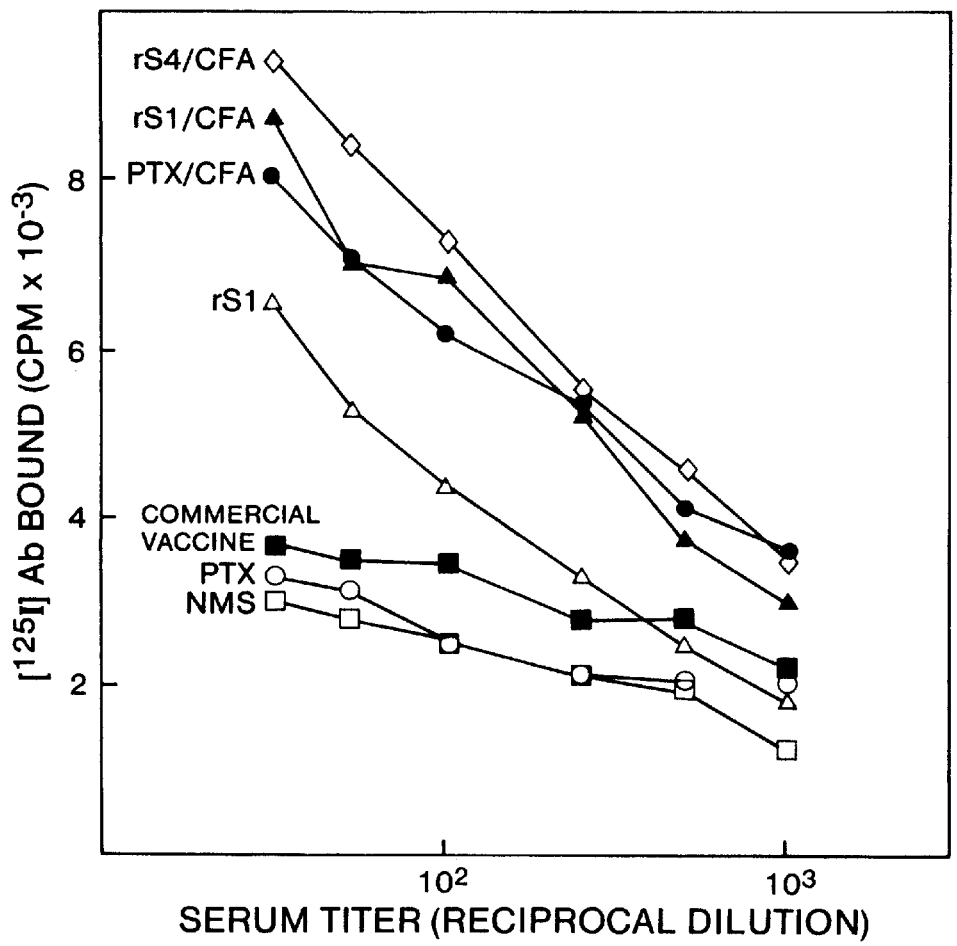
FIG. 5 is a graph of radioimmunoassays showing immunogenicity of rS1 and rS4 subunits in mice. Mice were hyperimmunized with recombinant S1, methionyl rS4, native pertussis toxin (PTX), commercial pertussis vaccine, or excipient (NMS); some preparations contained complete Freund's adjuvant (CFA). Sera were collected and dilutions were examined for their anti-PTX titer in a solid-phase radioimmunoassay.

When crude recombinant rS1 preparations were incubated in the presence of [$^{32}$P]NAD with membranes isolated from CHO cells, a protein of approximately 41,000 daltons was ADP-ribosylated, identical to that ribosylated by native whole PTX; this molecule is believed to be the $N_i$ membrane regulatory protein of the adenylate cyclase complex (Bokoch et al. 1983, J. Biol. Chem 258:2072–2075; and Hsia et al. 1983, J. Biol. Chem. 259:1086–1090). For purposes of routine assay, bovine transducin can be utilized as a substrate for the ribosylase (FIG. 4), a molecule demonstrated to be an acceptor for pertussis toxin-catalyzed ADP-ribose transfer from NAD. (Manning et al. supra; West et al., supra). This result confirms the location of the ADP-ribosyltransferase activity on the A protomer (S1 subunit) of the toxin and suggests that the recombinant B. pertussis protein is folded into a form close to its native three-dimensional structure in E. coli. Furthermore, the recombinant S1 exhibited NAD-glycohydrolase activity also identified with the A promoter. Mice were immunized and boosted by intraperitoneal injection with a crude inclusion-body preparation of rS1 or with purified recombinant methionyl S4. The rS1 subunit material used contained both fully-processed polypeptide and unprocessed preprotein in an approximate ratio of 1:2; the relative immunogenicity of the two rS1 species is not known. Serum samples were tested in a solid-phase RIA for the presence of antitoxin antibodies (FIG. 5). Animals receiving recombinant S1 exhibited a significant antitoxin response whether or not the immunizing doses were formulated with complete Freund's adjuvant. Recombinant S4, given only in adjuvanted form, was also very immunogenic relative to adjuvanted whole toxin and commercial pertussis vaccine.

Treatment of cultured CHO cells with whole pertussis toxin results in a "clustered" morphology (Hewlett et al., supra) that can be abrogated with antitoxin sera (Gellenius et al., supra). In preliminary experiments, mouse sera against rS1 or rS4, prepared as described above and possessing relatively high titers of antitoxin antibodies, was not routinely capable of neutralizing the response of CHO cells to native toxin.

Figure 6:
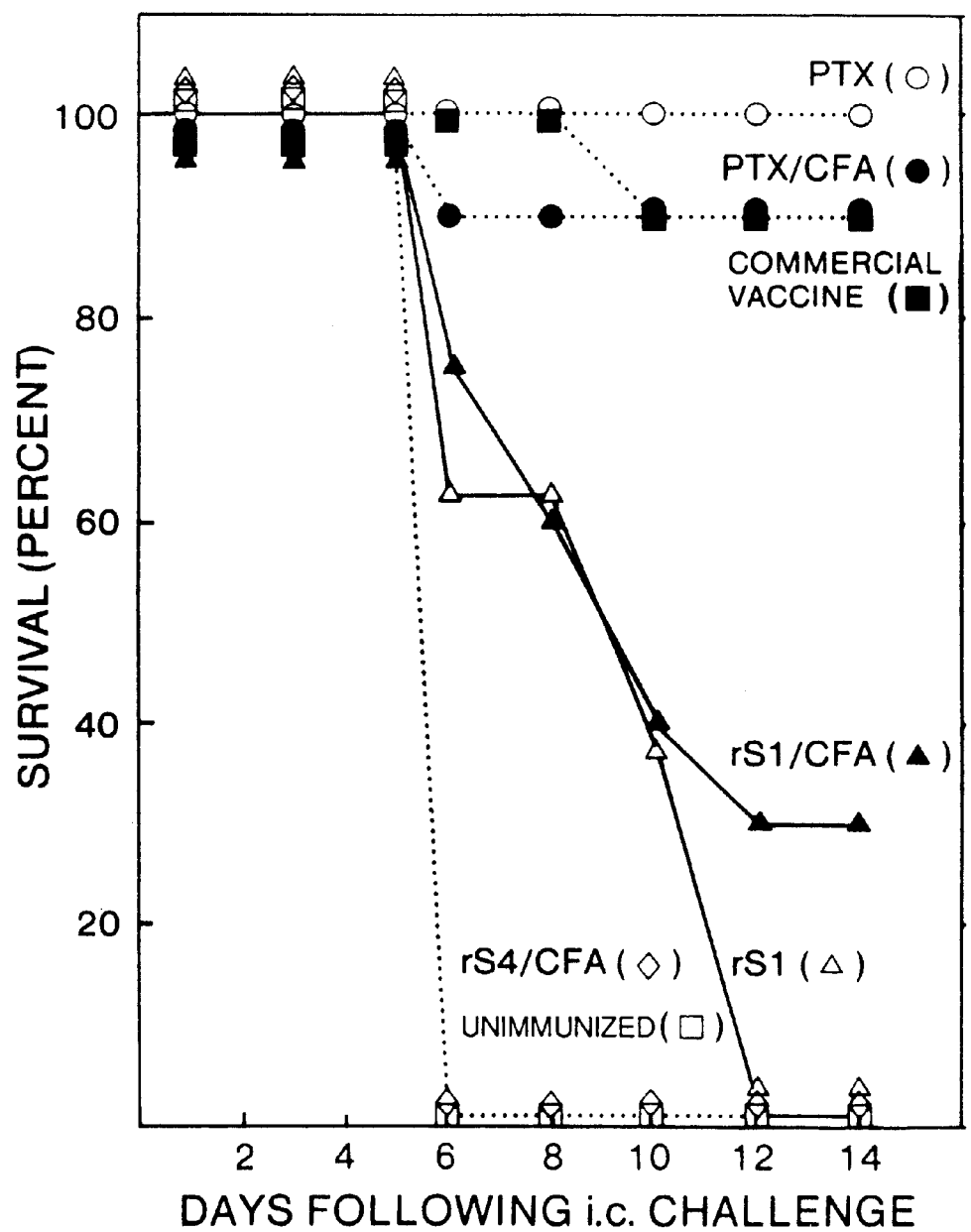
FIG. 6 is a graph demonstrating the immunoprotective potential of rS1 and rS4 in mice against i.c. challenge with B. pertussis. Details of the figure are given in the text.

Immunoprotection of mice with recombinant S1. Mice immunized with crude recombinant S1, purified recombinant S4, and appropriate control materials (see above) were subjected to intracerebral challenge (i.c.) with B. pertussis mouse virulent strain 18323 and mortality scored for as long as 45 days post-challenge (FIG. 6). Mice were immunized with 50 ug of test article (100 ul of a 1:35 dilution for commercial pertussis vaccine) by intraperitoneal injection; they were boosted with an identical amount 21 days post-inoculation and challenged 7 days later by i.c. challenge of viable B. pertussis strain 18323 ($3\times10^4$ organism per animal). Although protection was not expected because of the lack of active holotoxin in the recombinant preparations, it was surprising to observe an increase in survival time for rS1-immunized animals relative to unimmunized controls. Further, a number of mice receiving adjuvanted rS1 were completely protected against challenge; mice immunized with adjuvanted rS4, although exhibiting a good antibody response (see FIG. 5), were protected no better than unimmunized mice. In another preliminary experiment, adjuvanted rS1 appeared to elicit dose-responsive protection against challenge. Incomplete protection in the i.c. challenge assay may have its basis in an absence of active holotoxin in the immunizing material; nevertheless, protection achieved in this preliminary study demonstrates that recombinant S1 protein has potential as a subunit vaccine material. Later studies have not confirmed immunoprotection against intracerebral challenge with B. pertussis mouse virulent strain 18323.

S1 Analogs

Using techniques of protein engineering and site-specific mutagenesis, truncated S1 analogs were made. The region bounded by valine 7 and proline 14 was found to be a required region for ADP-ribosyltransferase activity of the S1 molecule. An antigenic epitope that binds a monoclonal antibody which passively-protects against toxin activity in mice (i.e., an epitope involved in eliciting a protective response) lies at least partially within the region bounded by valine 7 and proline, 14, inclusively. Mutagenesis of the S1 molecule in the region bounded by valine 7 and proline 14, inclusively, produced analog molecules of S1 lacking enzymatic activity while retaining the protective epitope. The protective epitope is important in providing immunoprotection against pertussis toxicity. Modification of the valine 7 through proline 14 region, including substitution and/or deletion of one or more amino acids, results in S1 analog products that can elicit toxin-neutralizing levels of antibodies and are substantially free of reactogenic components.

Subcloning of the PTX S1 gene into pUC18. Plasmid pPTX42, containing the entire operon for the *Bordetella pertussis* toxin (PTX), was obtained from J. Keith (NIAID, Rocky Mountain Laboratory) as transformed JM109 cells. The bacteria were grown in L-broth containing ampicillin and the plasmid recovered and purified by standard methods (Maniatis et al., supra). A 792-bp DNA fragment containing a portion of the PTX S1 gene (cistron) (Locht and Keith, supra) was isolated from pPTX42 by digestion of the plasmid with restriction enzymes AvaI and XbaI, followed by acrylamide gel electrophoresis and subsequent elution of the DNA fragment from the gel. This DNA fragment begins at the AvaI site just inside the open reading frame for the pre-S1 protein and ends at an XbaI site at the termination codon for S1. The standard cloning vector pUC18 was also digested with AvaI and XbaI and the digest treated with phosphatase. A ligation reaction was performed with the digested pUC18 vector, the 792-bp DNA fragment (AvaI-XbaI) of pPTX42, and T4 DNA ligase using standard conditions. Fresh competent DH52α cells were transformed with the ligation mixture and transformants were selected on agar plates of L-broth containing ampicillin and "Blue-gal" (Bethesda Research Laboratories, Gaithersburg, Md.). Twelve white colonies were selected, replica-plated, and grown as 2-ml liquid cultures. The cells were "miniprepped" by a standard alkaline lysis procedure, the DNA digested with AvaI and XbaI, and the digests subjected to acrylamide gel electrophoresis.

Construction of rPTXS1 expression plasmid pPTXS1/1. An AvaI-XbaI fragment of 792 bp was isolated from plasmid pPTX42 as previously described. *Escherichia coli* expression plasmids pCFM1156 and pCFM1036 were obtained from Charles F. Morris, Amgen Inc., Thousand Oaks, Calif. Plasmid pCFM1156 was digested with restriction enzymes SstI and NdeI and a 1.8 Kb DNA fragment was isolated from an agarose gel by electroelution onto NA45 paper (Schleicher & Schuell, Keene, N. H.). Plasmid pCFM1036 was digested with SstI and XbaI and a 2.8-Kb DNA fragment was likewise isolated. Two complementary strands of oligodeoxynucleotide linker, reconstituting the deleted portion of the S1 open reading frame, was synthetized by the aminophosphine chemistry of Caruthers et al. (supra). The sequence of the synthetic fragment, while maintaining the authentic amino acid sequence, was modified in its codon usage to reduce potential secondary structure in the messenger RNA; an exception to this was the substitution of a serine codon for the cysteine codon at amino acid position number 2 in the preprotein signal sequence order to eliminate any disulfide interactions between the preprotein signal and the two cysteine residues at positions 41 and 199 of the mature protein. This oligodeoxynucleotide linker had an NdeI site cohesive for the one in pCFM1156 and an AvaI cohesive end for ligation to the AvaI site of the 792-bp DNA fragment of the S1 gene. The sequence of this oligodeoxynucleotide was:

```
5'TATGCGTTCTAC3'           SEQ ID NO:7

3'ACGCAAGATGAGCC5'         SEQ ID NO:8
```

A ligation reaction was prepared with the 2.8-Kb DNA fragment of pCFM1036, the 1.8-Kb DNA fragment of pCFM1156, the 792-bp DNA fragment containing the S1 gene segment, the oligodeoxynucleotide linker, and T4 DNA ligase. After ligation, FM6 cells (obtained from C.F. Morris, Amgen Inc., Thousand Oaks, Calif.) were transformed with the ligation mixture and plated in L-broth agar with kanamycin. Colonies were selected and both replica-plated and miniprepped by the alkaline method (Maniatis et al., supra). Miniprepped DNA samples were subjected to restriction enzyme mapping and found to possess the expected DNA restriction fragments. The region from the beginning of the synthetic linker into the open reading frame of the authentic S1 gene was assessed by DNA sequence analysis. Subsequent induction of this plasmid led to high-level expression of recombinant S1 protein.

Construction of rPTXS1 expression plasmid pPTXS1/2. A DNA fragment of 181-bp was isolated from plasmid pPTXS1/1 by digestion with AccI and SphI; subsequent purification of the DNA fragment was on a polyacrylamide gel. This DNA fragment is an internal, left-hand portion of the S1 gene. Using the same procedures, a 564-bp DNA fragment representing the remaining right-hand portion of the gene was isolated from PTXS1 that was cloned into pUC18. This was accomplished by digestion of the plasmid with SphI and BamHI, the latter enzyme cutting downstream of the S1 cloning site (XbaI), at the BamHI site within the pUC18 cloning cluster. DNA fragments of 1.8 Kb and 2.8 Kb were isolated from the expression vector pCFM1156 by digestion with restriction enzymes NdeI, SstI, and BamHI, followed by isolation with agarose gel electrophoresis and electroelution of the DNA fragments. An oligodeoxynucleotide linker was synthesized; this double stranded linker had NdeI and AccI cohesive ends and the following sequence:

```
5'TATGGACGATCCACCTGCTACCGT3'     SEQ ID NO:9

3'ACCTGCTAGGTGGACGATGGCATA5'     SEQ ID NO:10
```

A ligation was performed by standard methods (Maniatis et al. supra) utilizing the 181-bp (AccI-SphI) and 564-bp (SphI-BamHI) DNA fragments from pPTXS1/1, the 1.8 Kb (NdeI-SstI) and 2.8 Kb (SstI-BamHI) DNA fragments from pCFM1156, the oligodeoxynucleotide linker, and T4 DNA ligase. Following ligation, the mixture was used to transform fresh, competent FM5 cells. Kanamycin-resistant transformants were obtained, restriction enzyme analyses performed on minipreps of plasmid DNA, and the structure confirmed by DNA sequences analysis of the junctions.

Bal31 digestion of pPTXS1/2 and construction of vectors with truncated S1 genes. To assess important antigenic epitopes and enzymatically-active sites near the amino-terminal end of the mature S1 molecule, truncated versions of this protein were made. The expression plasmid pPTXS1/2 was digested with NdeI, treated with the exonuclease Bal31 (IBI) under standard conditions, and aliquots removed at various times up to 110 min. Following inactivation of Bal31 for 15 min at 65° C., samples were analyzed for increases in electrophoretic migration by electrophoresis on agarose gels. Samples from the aliquots at 100 min and 110 min were pooled (fraction A) and the remaining samples pooled and digested with additional Bal31; aliquots were removed at various times up to 180 min. After quenching the reaction, aliquots were again examined for increases in electrophoretic migration and four additional fractions (B, C, D, and E) were retained. Each of the five fractions was individually digested with SstI and DNA fragments of 3–3.5 Kb were isolated from agarose gels by electroelution.

Expression vector pCFM1156 was digested with SstI and HpaI, and a 1.8-Kb DNA fragment likewise isolated. The individual 3–3.5 Kb DNA fragments (Bal31 blunt-SstI) from pPTXS1/2 each were ligated with the 1.8-Kb DNA fragment (SstI-HpaI) using T4 DNA ligase under standard conditions. Fresh., competent FM5 cells were transformed with each individual ligation mixture and kanamycin-resistant transformants isolated. Transformants each of fraction A and B truncations were picked, minipreps induced at 42° C., and the preparations examined by light microscopy for the presence of inclusion bodies. Inclusion-positive preparations were miniprepped, digested with XbaI, and the DNA inserts examined for size by agarose gel electrophoresis. Samples ranging in size from 600–650 bp were selected for DNA sequencing to confirm the structure of the truncations. Subsequent analyses of the expressed recombinant proteins indicated that a required region for ADP-ribosyltransferase activity of the S1 molecule and an epitope involved in eliciting a protective response (i.e., an antigenic epitope that binds a monoclonal antibody which passively protects against toxin activity in mice) lies within a region bounded inclusively by valine 7 and proline 14 (for full amino-acid sequence, see Locht and Keith, supra) of the mature molecule. These truncated versions of the S1 molecule, by virtue of the vector construction, all begin at their N-termini with methionylvalyl followed by the truncated sequence.

Mutagenesis of S1. In order to fine-map the region bounded by valine 7 and proline 14 and to produce analog molecules of S1 lacking enzymatic activity while retaining the protective epitope in this region, the recombinant S1 gene was subjected to mutagenesis. Retention of the protective epitope is defined by reactivity with monoclonal antibody 1B7. This was accomplished by substituting synthetic oligodeoxynucleotide segments for the authentic region encoding the residues valine 7 through proline 14. These segments contained single or double codon substitutions in order to modify the authentic amino acid sequence. Modification can be achieved by deletion and/or substitution. It is within the scope of the present invention to modify a single base to obtain the desired characteristics of the S1 analogs. A single base can be modified in order to modify the amino acid sequence. However, it is recognized by those skilled in the art that the statistical likelihood of genotypic reversion to wild type is greater when a single base is modified as compared to modification of at least two bases. Therefore, in a preferred embodiment, each of these codon changes involved the substitution of at least two bases in each codon to reduce the efficiency of reversions. The oligodeoxynucleotide linkers were synthesized with AccI and BspMII cohesive ends and contained the authentic S1 sequence, except for the codon changes noted in the linker descriptions in Table I:

TABLE I construct: pPTXS1(6A-3/5-1)
codon change: tyr8 to phe
oligodeoxynucleotide linker sequence:

| | |
|---|---|
| 5'ATTCCGCTATGACTCCCGCCCG3' | SEQ ID NO:11 |
| 3'AGGCGATACTGAGGGCGGGCGGCC5' | SEQ ID NO:12 | construct: pPTXS1(6A-3/4-1)
codon change: arg9 to lys
oligodeoxynucleotide linker sequence:

| | |
|---|---|
| 5'ATACAAGTATGACTCCCGCCCG3' | SEQ ID NO:13 |
| 3'TGTTCATACTGAGGGCGGGCGGCC5' | SEQ ID NO:14 | construct: pPTXS1(6A-3/3-1)
codon change: asp11 to glu
oligodeoxynucleotide linker sequence:

TABLE I-continued

| | |
|---|---|
| 5'ATACCGCTATGAATCCCGCCCG3' | SEQ ID NO:15 |
| 3'TGGCGATACTTAGGGCGGGCGGCC5' | SEQ ID NO:16 | construct: pPTXS1(6A-3/2-2)
codon change: ser12 to gly
oligodeoxynucleotide linker sequence:

| | |
|---|---|
| 5'ATACCGCTATGACGGCCGCCCG3' | SEQ ID NO:17 |
| 3'TGGCGATACTGCCGGCGGGCGGCC5' | SEQ ID NO:18 | construct: pPTXS1(6A-3/1-1)
codon change: arg13 to lys
oligodeoxynucleotide linker sequence:

| | |
|---|---|
| 5'ATACCGCTATGACTCCAAGCCG3' | SEQ ID NO:19 |
| 3'TGGCGATACTGAGGTTCGGCGGCC5' | SEQ ID NO:20 | construct: pPTXS1(6A-3/8-1)
codon change: tyr8 to leu and arg9 to glu
oligodeoxynucleotide linker sequence:

| | |
|---|---|
| 5'ATTGGAATATGACTCCCGCCCG3' | SEQ ID NO:21 |
| 3'ACCTTATACTGAGGGCGGGCGGCC5' | SEQ ID NO:22 | construct: pPTXS1(6A-3/7-2)
codon change: arg9 to asn and ser12 to gly
oligodeoxynucleotide linker sequence:

| | |
|---|---|
| 5'ATACAACTATGACGGCCGCCCG3' | SEQ ID NO:23 |
| 3'TGTTGATACTGCCGGCGGGCGGCC5' | SEQ ID NO:24 | construct: pPTXS1(6A-3/6-1)
codon change: asp11 to pro and pro14 to asp
oligodeoxynucleotide linker sequence:

| | |
|---|---|
| 5'ATACCGCTATCCGTCCCGCGAC3' | SEQ ID NO:25 |
| 3'TGGCGATAGGCAGGGCGCTGGGCC5' | SEQ ID NO:26 |

For expression-plasmid construction, the following DNA fragments were isolated by electroelution from agarose gels:
1) an 1824-bp DNA fragment (AccI to SstI) from pPTXS1 (6A), a plasmid constructed as previously described which expressed a recombinant S1 analog molecule that has deleted aspartate 1 and aspartate 2 and is substituted with methionylvalyl;
2) a 3.56-Kb DNA fragment (SstI to BspMII) from pPTXS1(33B), a plasmid constructed as previously described which expressed a recombinant S1 analog that has deleted the first fourteen amino acid residues and substituted a methionylvalyl. In this particular gene construction, the blunt-end ligation that resulted in this foreshortened molecule created a new BspMII site. This restriction site, not present in the native S1 cistronic element, allowed the utilization of relatively short oligonucleotide linkers with AccI and BspMII cohesive ends to effect the mutagenesis.

These two DNA fragments were ligated with the individual oligodeoxynucleotide fragments described above under standard ligation conditions. These ligations resulted in newly constructed S1 genes: a portion of pPTXS1(6A) providing the upstream codons to the point of the AccI restriction site, the synthetic fragments providing the various mutations to codons between the AccI site and the BspMII site, and a portion of pPTXS1(33B) providing the remainder of the S1 coding region downstream of the novel BspMII restriction site. Following ligation, each mixture was used to transform a separate preparation of fresh, competent FM5 cells. Transformants were picked, grown as minipreps, induced to produce recombinant protein, and inclusion body-positive samples identified by light microscopy. These samples were fermented at a larger scale (1–6 liters) at the induction temperature to prepare greater amounts of each recombinant analog protein. Isolated cell pastes were lysed in a French press after resuspension in distilled $H_2O$ with 1 mM DTT. Inclusion bodies were isolated from these lysates by simple low-speed centrifugation. These inclusion-body protein preparations contained as little as 30% and as much as 80% of the recombinant proteins. Each preparation was analyzed for its ability to bind in a Western blot format (Burnette, supra.) to monoclonal antibody B2F8 directed against a dominant epitope identified in our studies with truncated S1 analogs, and to bind to monoclonal antibody 1B7 known to passively protect mice against intracerebral challenge with virulent B. pertussis (Sato et al. supra). The samples were also assessed for ADP-ribosyltransferase activity. The results obtained are shown in Table 2.

TABLE 2

| Sample | Antibody Binding | | ADP-RTase Activity |
| --- | --- | --- | --- |
| | B2F8 | 1B7 | |
| none | − | − | − |
| PTX (commercial) | + | + | + |
| rPTXS (PPTXS1/1) | + | + | + |
| pPTXS1 (6A-3/1-1) | + | + | + |
| pPTXS1 (6A-3/2-2) | + | + | + |
| pPTXS1 (6A-3/3-1) | + | + | + |
| pPTXS1 (6A-3/4-1) | + | + | − |
| pPTXS1 (6A-3/5-1) | + | + | + |
| pPTXS1 (6A-3/6-1) | − | − | − |
| pPTXS1 (6A-3/7-2) | − | − | − |
| pPTXS1 (6A-3/8-1) | − | − | − |

Figure 8A:
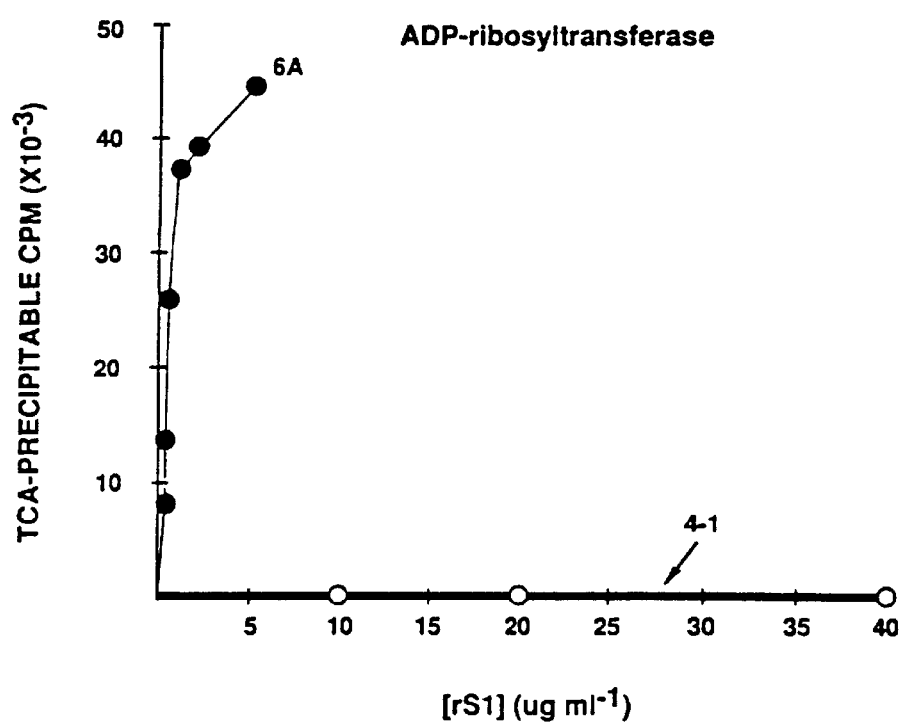
FIGS. 8A and 8B are graphs of ADP-ribosyltranfease and NAD glycohdrolase activity of recombinant analog S1.
Figure 8B:
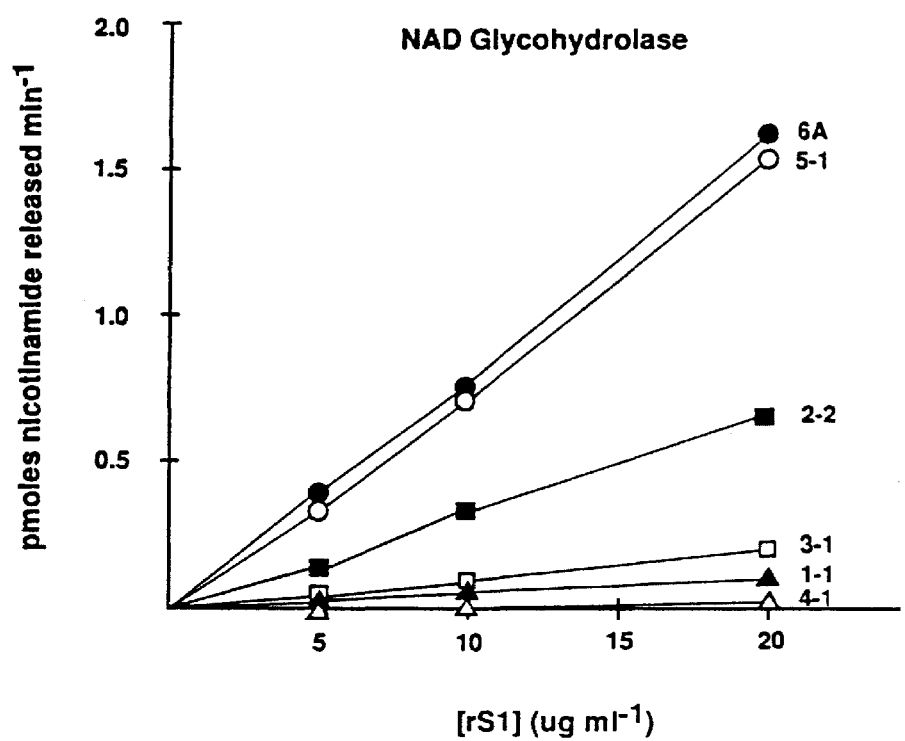

The S1 analog 4-1 (Arg9-Lys) exhibited little or no transferase activity while retaining reactivity with neutralizing mAb 1B7. Only extremely small amounts of enzymatic activity could be revealed by increasing the amount of 4-1 protein in the assay (FIG. 8A); repeated determinations indicated that the specific ADP-ribosyltransferase activity of the S1 analog was reduced by a factor of at least 5,000. Measurement of the NAD glycohydrolase activity associated with the single-residue substitution mutants (FIG. 8B) revealed a pattern similar to that obtained from evaluation of ADP-ribosyltransferase activity. S1 analog 4-1 exhibited little or no detectable glycohydrolase activity, indicating a reduction in the magnitude of this activity by a factor of at least 50 to 100.

Because of its ability to retain binding to a passively-protective monoclonal antibody (i.e., retaining a major protective epitope) and to lack a major marker of toxic activity (ADP-ribosyltransferase), the recombinant S1 analog molecule produced by clone pPTXS1(6A-3/4-1), as shown in FIG. 7 and modifications thereof, have application as safe, economical subunit vaccines, either alone or in combination with other PTX subunits. The S1 analogs produced by clone pPTXS1(6A-3/4-1), wherein lysine is substituted for arginine 9, is illustrative of rS1 analogs having the desired properties necessary for safe subunit vaccines. Other analogs of 6A-3/4-1 could include, for example, aspartylaspartyl residues at positions 1 and 2, methionylaspartylaspartyl residues at positions 0, 1 and 2, and methionylvalylaspartyl residues at positions 0, 1 and 2.

Current acellular vaccines contain S1, S2, S3, S4, and S5 subunits. The morphological modification produced in cultured mammalian cells by pertussis toxin has recently been shown to be a property of the S1 subunit (Burns et al., 1987, Infect. Immun. 55:24–28.), although this effect has only been demonstrated in the presence of the B oligomer. Preliminary studies described herein demonstrate the feasibility of a single subunit vaccine utilizing rS1 analogs that retain a major protective epitope but lack toxic activity. S1 analogs also have application in combination with subunits S2, S3, S4 and S5. These subunits may augment the immune response to S1 and may themselves have protective epitopes. It is within the scope of this invention that vaccines comprising S1 subunit analogs can further include at least one of said subunits S2, S3, S4, 5, and mixtures thereof, of Bordetella exotoxin. The S2, S3, S4, S5 can be subunits derived from B. pertussis, or genetically-engineered subunits and their analogs. Genetically-engineered subunit products can include fusion proteins and non-fusion proteins.

For purposes of the experiments described in the following section, we modified the expression system to produce an S1 subunit analog (S1/1-4) which possesses the lysine-for-arginine 9 substitution, but which also possesses the native aspartylaspartate residues at its amino terminus.

Assessment of Biological Activity of the S1/1-4 Analogs and S1/1

Figure 9:
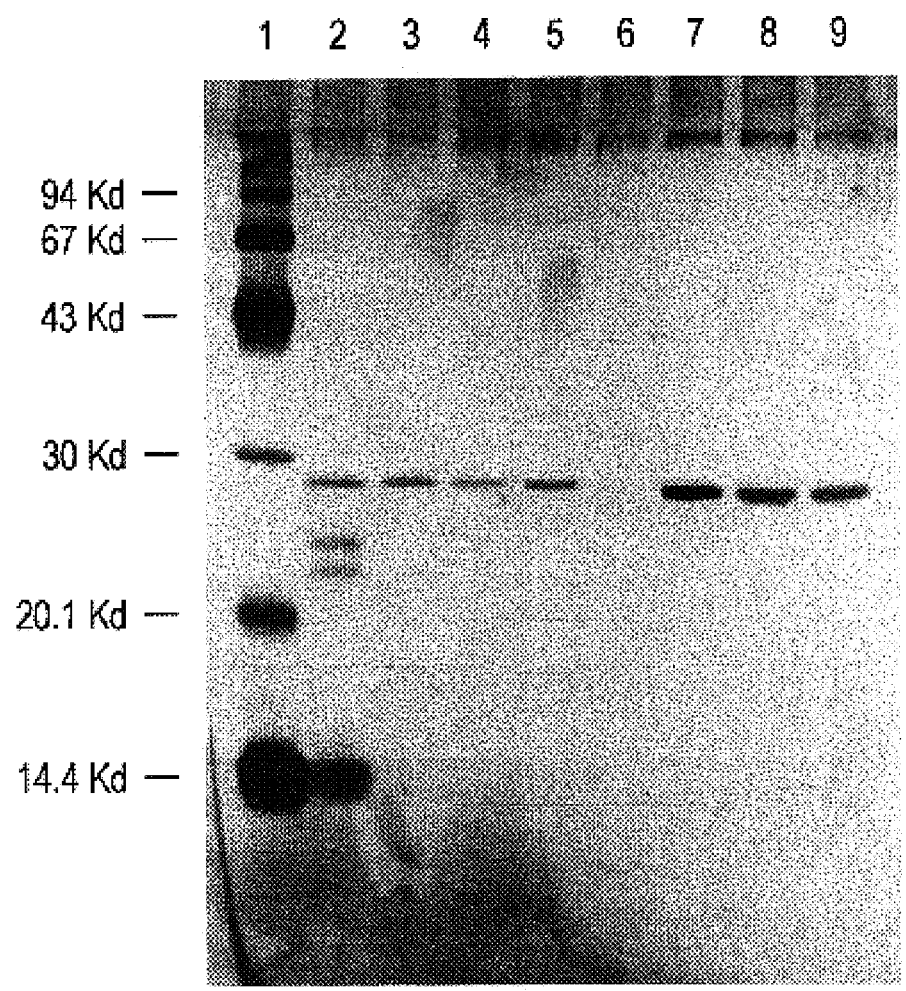
FIG. 9 is an autoradiogram of a SDS-polyacrylamide gel of purified S1 subunit proteins

Recombinant S1 protein of native sequence (S1/1) and analog S1/1-4 (as described above, contains the Arg 9-Lys substitution and the aspartylaspartate amino terminal residues of the native sequence) were individually isolated from the E. coli producer cells by a procedure which included cell disruption, centrifugation, urea solubilization, ion exchange chromatography, and gel filtration chromatography. The cell pastes were suspended in 25 mM Tris buffer, pH 8.5, and lysed by high-pressure disruption (French press). The lysates were centrifuged and the insoluble pellets, which contained the recombinant S1 proteins, were solubilized in 8 M urea, 25 mM Tris, pH8.5. Following the addition of $CuSO_4$ to a concentration of 50 uM, the mixtures were stirred overnight to allow the formation of disulfide bonds in the recombinant S1 proteins. The mixtures were diluted with an equal volume of 8 M urea, 25 mM sodium citrate, pH 3.8, and applied to columns of S-Sepharose ("fast-flow") equilibrated at pH 3.8 in 8 M urea. The columns were eluted with linear gradients of NaCl (0–0.5 M) in 8 M urea, 12.5 mM sodium citrate, pH 3.8. Broad peaks were collected from each column and titrated to pH 7.5. These pools of chromatographic fractions were applied separately to Sephacryl S-200 columns equilibrated in 2 M urea, 10 mM potassium phosphate, pH 7.5, and pools of eluting material were collected that represented oxidized, monomeric recombinant S1 proteins of each species (S1/1 and S1/1-4). Purified S1 subunit proteins were analyzed by SDS-PAGE followed by silver-staining of the proteins in the gels (FIG. 9). Gels (12.5% acrylamide) were run under reducing conditions. Lane 1, molecular weight standards (Pharmacia). Lane 2, 2 ug of B. pertussis holotoxin (List Biological Laboratories). Lane 3, 0.2 ug of B. pertussis S1 subunit protein (List Biological Laboratories). Lane 4, 0.2 ug of recombinant S1/1. Lane 5, 0.2 ug of recombinant S1/1-4. Lane 6, blank. Lane 7, 0.4 ug of S1 subunit protein (List). Lane 8, 0.4 ug of recombinant S1/1. Lane 9, 0.4 ug of recombinant S2/1-4. At this stage of preparation, the recombinant S1 species were greater than 90% pure.

Figure 10:
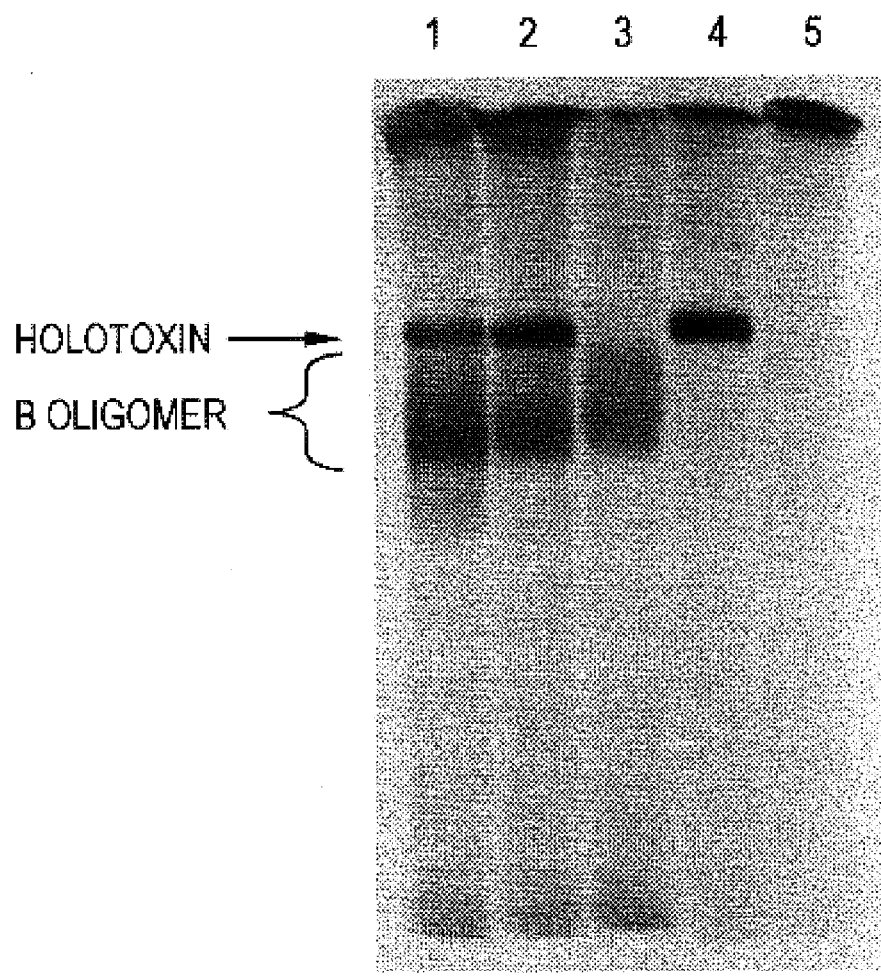
FIG. 10 is an autoradiogram of a native, non-reducing, non-denaturing polyacrylamide gel of holotoxins from the combination of native B oligomer with either recombinant S1/1 or recombinant S1/1-4.
Figure 11G:
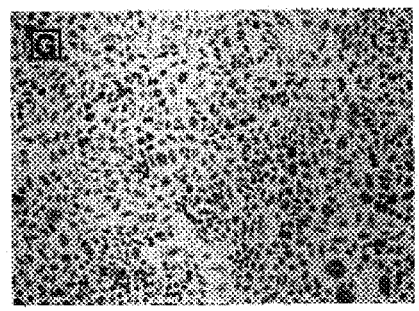
Figure 11H:
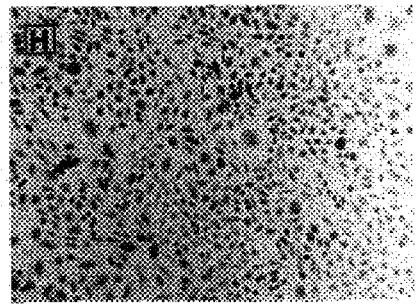
Figure 11I:
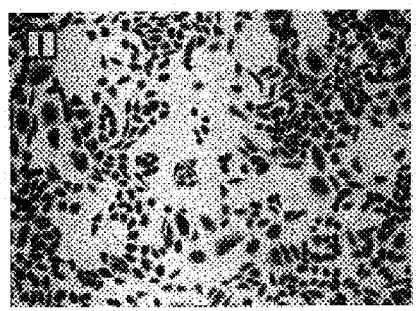
Figure 11J:
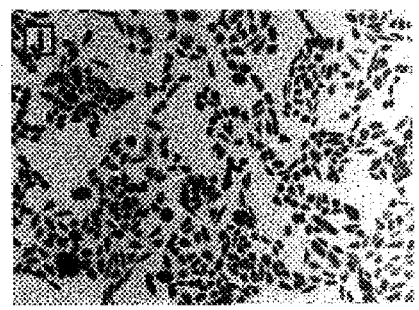

To assess the biological activity of the S1 Arg9-Lys mutation, it was necessary to achieve the association of the mutant analog and the recombinant S1 protein of native sequence into pertussis holotoxin species. Highly purified pertussis toxin B oligomer (a pentameric structure of toxin subunits S2, S3, S4, and S5) was provided by D. Burns, Center for Biologics Evaluation and Research, Food and Drug Administration, The two different S1 subunit species were allowed to individually associate with the B oligomer to form holotoxin molecules (containing either S1/1 or S1/1-4) by the following procedure. Equal molar amounts of recombinant S1 species and B oligomer were combined in solutions of 2 M urea, 10 mM potassium phosphate, pH 7.5, and were incubated for 30 min at 37° C. Holotoxin formation was assessed by electrophoresis in native acrylamide gels (FIG. 10). Gel 1, recombinant S1/1 and native oligomer. Gel 2, recombinant S1/1-4 and native B oligomer. Gel 3, native B oligomer. Gel 4, native *B. pertussis* holotoxin. Gel 5, recombinant S1/1. The gels indicate that holotoxin species were assembled from the combination of native B oligomer with either recombinant S1/1 or recombinant S1/1-4.

Semi-recombinant holotoxins (B oligomer plus either S1/1 or analog S1.1-4) were then examined for their ability to elicit a clustering response in Chinese hamster ovary (CHO) cells in in vitro; this response has been shown to be a measure of the cytopathicity of pertussis toxin. Experimental samples and appropriate control samples were diluted into CHO cell culture medium (Dulbecco modified Eagle medium with 10% fetal bovine serum), sterilized by ultrafiltration, and further diluted by serial transfer in 96-well plastic culture dishes. Approximately $5-7 \times 10^3$ freshly-trypsinized CHO cells (American Type Culture Collection CCL 61, CHO-K1 cells) were added to each well and the dishes incubated at 37° C. in 5% $CO_2$ for 48–72 hours. The cell monolayers were washed with phosphate-buffered saline, stained with crystal violet, and examined for the presence of cell clusters by light microscopy.

FIG. 11 illustrates the results of such analyses; of particular interest are the results of Panels G, H and J, relating to the S1/1-4 analog. The S1/1-4 analog alone and the 1/1600 dilution of holotoxin formed from S1/1-4 analog and B oligomer demonstrate a lack of cell clustering, with the 1/200 dilution exhibiting a negligible amount of clustering. Panel A are cells treated with a 1/200 dilution of buffer only. Panel B is treatment with B oligomer only, at a dilution of 1/200; some small amount of clustering is visible at this dilution and is attributable to contaminating native S1 subunit remaining after purification. Panel B can be compared with another field of this same well (Panel I), clearly showing clustering activity of the B oligomer preparation at a dilution of 1/200. Panel C are cells treated with native, commercial-grade S1 subunit (List Biologicals) at 1/2000 dilution. Panel D is native, commercial-grade pertussis holotoxin (List Biologicals) at 1/2000 dilution, demonstrating the dramatic cytopathic effect of pertussis toxin on CHO cells in culture. Panel E is recombinant S1 subunit of native sequence (S1/1) at a dilution of 1/2000. Panel F shows S1/1 combined with B oligomer and diluted to 1/2000; the effect of CHO cell clustering appears just as dramatic as with native holotoxin and supports the physical gel results (above) showing holotoxin association with B oligomer and the recombinant S1 protein. Panel G illustrates that Arg9-Lys mutant S1/1-4 by itself has no effect on the CHO cells. Panel H shows the lack CHO cell clustering at a 1/1600 dilution of holotoxin formed from the S1/1-4 analog and B oligomer. At a dilution of 1/200 (Panel J), some clustering by the S1/1-4-containing holotoxin can be seen; however, the contribution to the clustering effect by the analog S1 species appears negligible when compared to B oligomer by itself at the same dilution (Panel I).

Initial experiments have been made to quantitate the effective concentration of the various pertussis toxin species required to elicit the CHO cell clustering phenomenon. Preliminary results indicate that both commercial pertussis toxin and holotoxin containing recombinant S1/1 can cause cell clustering at concentrations as low as 0.25–0.30 ng/ml; in contrast, holotoxin containing the S1/1-4 analog is required at concentrations of at least 10–25 ng/ml in order to induce the clustering effect.

These results confirm that the cytotoxic effect of pertussis toxin resides in its S1 subunit moiety and that it is directly related to its enzymatic activities. More importantly, these experiments demonstrate that a relatively non-toxic pertussis toxin molecule can be formed from specific recombinant toxin subunits derived by site-directed mutagenesis.

It is intended that the present invention include all such modifications and improvements as come within the scope of the present invention as claimed.

What is claimed is:

1. A polypeptide analog of *Bordetella pertussis* toxin S1 subunit, said analog differing in the amino acid sequence from that of naturally occurring S1 subunit by substitution of a different amino acid residue at arginine 9, wherein the analog has a biological activity which (a) can elicit toxin-neutralizing levels of antibodies and (b) is substantially free of enzymatic activities associated with toxin reactogenicity.

2. The analog of claim 1 wherein said toxin-neutralizing levels of antibodies provide immunoprotection against *Bordetella* toxicity.

3. The analog of claim 1 wherein said biological activity of (b) is obtained by site-specific mutagenesis resulting in said analog being substantially inactive enzymatically.

4. The analog of claim 1 wherein said arginine 9 is replaced with lysine.

5. The analog of claim 1 which includes an amino-terminus methionylvalyl sequence.

6. An analog of *Bordetella pertussis* toxin S1 subunit, said analog comprising an amino acid sequence as depicted in FIG. 7 (SEQ ID NO: 27), said analog having a biological activity which (a) can elicit toxin-neutralizing levels of antibodies and (b) is substantially free of enzymatic activities associated with toxin reactogenicity.

7. A vaccine against pertussis comprising a modified *Bordetella pertussis* toxin in which a different amino acid residue has been substituted for arginine 9 in subunit S1, wherein the modified *Bordetella pertussis* toxin has a biological activity which (a) can elicit toxin-neutralizing levels of antibodies and (b) is substantially free of enzymatic activities associated with toxin reactogenicity.

8. The vaccine of claim 7 wherein said toxin-neutralizing levels of antibodies provide immunoprotection against *Bordetella* toxicity.

9. The vaccine of claim 7 wherein arginine 9 is replaced with lysine.

10. A vaccine against pertussis comprising a polypeptide analog of *Bordetella pertussis* toxin subunit S1 comprising an amino acid sequence depicted in FIG. 7 (SEQ ID NO: 27), said analog having a biological activity which (a) can elicit toxin-neutralizing levels of antibodies and (b) is substantially free of enzymatic activities associated with toxin reactogenicity.

11. An immunoprotective *Bordetella pertussis* toxin S1 subunit analog wherein at least arginine at the ninth position from the mature N-terminus in the S1 subunit has been substituted with a different amino acid to reduce the toxicity without adversely affecting the immunological properties, and wherein the toxin S1 subunit analog is produced by the process of a) site-directed mutagenesis of the native pertussis toxin S1 subunit gene and b) expression of said gene mutated by site-directed mutagenesis.

12. The *Bordetella pertussis* toxin S1 subunit analog of claim 11 in which lysine has been substituted for said arginine.

13. A vaccine against *Bordetella pertussis*, comprising an effective amount of an immunoprotective, genetically-detoxified *Bordetella pertussis* toxin comprising an S1 subunit analog wherein at least arginine at the ninth position from the mature N-terminus in the S1 subunit has been substituted with a different amino acid, thereby reducing the ADP-ribosyltransferase activity of the S1 subunit, and wherein said vaccine is produced by the process of a) site-directed mutagenesis of the native pertussis toxin S1 subunit gene, b) expression of said gene mutated by site-directed mutagenesis, and c) incorporation of the S1 subunit analog into a toxin molecule.

14. The vaccine of claim 13 in which lysine has been substituted for said arginine.

15. A vaccine comprising a *Bordetella pertussis* toxin S1 subunit analog in which at least the arginine residue at the ninth position from the mature N-terminus in the S1 subunit sequence has been substituted with another amino acid, wherein the S1 subunit analog, when expressed, is recognized by an antibody that confers immunoprotection against *Bordetella pertussis* and lacks enzymatic activity associated with *Bordetella pertussis* toxin reactogenicity, wherein the S1 subunit is produced by the process of a) site-directed mutagenesis of the native *Bordetella pertussis* toxin S1 subunit gene, and b) incorporation of said gene mutated by site-directed mutagenesis into a bacterial cell.

16. The vaccine of claim 15 in which lysine has been substituted for said arginine.

17. A polypeptide analog of the S1 subunit of *Bordetella pertussis*, said analog differing in amino acid sequence from that of the native S1 subunit sequence by at least one amino acid substitution including the substitution of a different amino acid residue at the arginine-9 position.

18. The polypeptide analog of claim 17 wherein arginine is replaced with lysine at the arginine-9 position.

* * * * *

SEQUENCE LISTING

```
<160> NUMBER OF SEQ ID NOS: 27

<210> SEQ ID NO 1
<211> LENGTH: 12
<212> TYPE: DNA
<213> ORGANISM: Artificial
<220> FEATURE:
<223> OTHER INFORMATION: Synthesized oligodeoxynucleotide

<400> SEQUENCE: 1
catcgattct ag                                                          12

<210> SEQ ID NO 2
<211> LENGTH: 20
<212> TYPE: DNA
```

```
<213> ORGANISM: Artificial
<220> FEATURE:
<223> OTHER INFORMATION: Synthesized oligodeoxynucleotide

<400> SEQUENCE: 2
tgcagtagct aagatcttaa                                              20

<210> SEQ ID NO 3
<211> LENGTH: 10
<212> TYPE: DNA
<213> ORGANISM: Artificial
<220> FEATURE:
<223> OTHER INFORMATION: Synthesized oligodeoxynucleotide

<400> SEQUENCE: 3
cgatttgatt                                                         10

<210> SEQ ID NO 4
<211> LENGTH: 12
<212> TYPE: DNA
<213> ORGANISM: Artificial
<220> FEATURE:
<223> OTHER INFORMATION: Synthesized oligodeoxynucleotide

<400> SEQUENCE: 4
taaactaaga tc                                                      12

<210> SEQ ID NO 5
<211> LENGTH: 46
<212> TYPE: DNA
<213> ORGANISM: Artificial
<220> FEATURE:
<223> OTHER INFORMATION: Synthesized oligodeoxynucleotide

<400> SEQUENCE: 5
ctagaaggaa ggaataacat atggttaacg cgttggaatt cggtac                 46

<210> SEQ ID NO 6
<211> LENGTH: 38
<212> TYPE: DNA
<213> ORGANISM: Artificial
<220> FEATURE:
<223> OTHER INFORMATION: Synthesized oligodeoxynucleotide

<400> SEQUENCE: 6
ttccttcctt attgtatacc aattgcgcaa ccttaagc                          38

<210> SEQ ID NO 7
<211> LENGTH: 12
<212> TYPE: DNA
<213> ORGANISM: Artificial
<220> FEATURE:
<223> OTHER INFORMATION: Synthesized oligodeoxynucleotide

<400> SEQUENCE: 7
tatgcgttct ac                                                      12

<210> SEQ ID NO 8
<211> LENGTH: 14
<212> TYPE: DNA
<213> ORGANISM: Artificial
<220> FEATURE:
<223> OTHER INFORMATION: Synthesized oligodeoxynucleotide

<400> SEQUENCE: 8
acgcaagatg agcc                                                    14
```

<210> SEQ ID NO 9
<211> LENGTH: 24
<212> TYPE: DNA
<213> ORGANISM: Artificial
<220> FEATURE:
<223> OTHER INFORMATION: Synthesized oligodeoxynucleotide

<400> SEQUENCE: 9
tatggacgat ccacctgcta ccgt                                        24

<210> SEQ ID NO 10
<211> LENGTH: 24
<212> TYPE: DNA
<213> ORGANISM: Artificial
<220> FEATURE:
<223> OTHER INFORMATION: Synthesized oligodeoxynucleotide

<400> SEQUENCE: 10
acctgctagg tggacgatgg cata                                        24

<210> SEQ ID NO 11
<211> LENGTH: 22
<212> TYPE: DNA
<213> ORGANISM: Artificial
<220> FEATURE:
<223> OTHER INFORMATION: Synthesized oligodeoxynucleotide

<400> SEQUENCE: 11
attccgctat gactcccgcc cg                                          22

<210> SEQ ID NO 12
<211> LENGTH: 24
<212> TYPE: DNA
<213> ORGANISM: Artificial
<220> FEATURE:
<223> OTHER INFORMATION: Synthesized oligodeoxynucleotide

<400> SEQUENCE: 12
aggcgatact gagggcgggc ggcc                                        24

<210> SEQ ID NO 13
<211> LENGTH: 22
<212> TYPE: DNA
<213> ORGANISM: Artificial
<220> FEATURE:
<223> OTHER INFORMATION: Synthesized oligodeoxynucleotide

<400> SEQUENCE: 13
atacaagtat gactcccgcc cg                                          22

<210> SEQ ID NO 14
<211> LENGTH: 24
<212> TYPE: DNA
<213> ORGANISM: Artificial
<220> FEATURE:
<223> OTHER INFORMATION: Synthesized oligodeoxynucleotide

<400> SEQUENCE: 14
tgttcatact gagggcgggc ggcc                                        24

<210> SEQ ID NO 15
<211> LENGTH: 22
<212> TYPE: DNA
<213> ORGANISM: Artificial
<220> FEATURE:

```
<223> OTHER INFORMATION: Synthesized oligodeoxynucleotide

<400> SEQUENCE: 15
ataccgctat gaatcccgcc cg                                              22

<210> SEQ ID NO 16
<211> LENGTH: 24
<212> TYPE: DNA
<213> ORGANISM: Artificial
<220> FEATURE:
<223> OTHER INFORMATION: Synthesized oligodeoxynucleotide

<400> SEQUENCE: 16
tggcgatact tagggcgggc ggcc                                            24

<210> SEQ ID NO 17
<211> LENGTH: 22
<212> TYPE: DNA
<213> ORGANISM: Artificial
<220> FEATURE:
<223> OTHER INFORMATION: Synthesized oligodeoxynucleotide

<400> SEQUENCE: 17
ataccgctat gacggccgcc cg                                              22

<210> SEQ ID NO 18
<211> LENGTH: 24
<212> TYPE: DNA
<213> ORGANISM: Artificial
<220> FEATURE:
<223> OTHER INFORMATION: Synthesized oligodeoxynucleotide

<400> SEQUENCE: 18
tggcgatact gccggcgggc ggcc                                            24

<210> SEQ ID NO 19
<211> LENGTH: 22
<212> TYPE: DNA
<213> ORGANISM: Artificial
<220> FEATURE:
<223> OTHER INFORMATION: Synthesized oligodeoxynucleotide

<400> SEQUENCE: 19
ataccgctat gactccaagc cg                                              22

<210> SEQ ID NO 20
<211> LENGTH: 24
<212> TYPE: DNA
<213> ORGANISM: Artificial
<220> FEATURE:
<223> OTHER INFORMATION: Synthesized oligodeoxynucleotide

<400> SEQUENCE: 20
tggcgatact gaggttcggc ggcc                                            24

<210> SEQ ID NO 21
<211> LENGTH: 22
<212> TYPE: DNA
<213> ORGANISM: Artificial
<220> FEATURE:
<223> OTHER INFORMATION: Synthesized oligodeoxynucleotide

<400> SEQUENCE: 21
attggaatat gactcccgcc cg                                              22
```

```
<210> SEQ ID NO 22
<211> LENGTH: 24
<212> TYPE: DNA
<213> ORGANISM: Artificial
<220> FEATURE:
<223> OTHER INFORMATION: Synthesized oligodeoxynucleotide

<400> SEQUENCE: 22
accttatact gagggcgggc ggcc                                              24

<210> SEQ ID NO 23
<211> LENGTH: 22
<212> TYPE: DNA
<213> ORGANISM: Artificial
<220> FEATURE:
<223> OTHER INFORMATION: Synthesized oligodeoxynucleotide

<400> SEQUENCE: 23
atacaactat gacggccgcc cg                                                22

<210> SEQ ID NO 24
<211> LENGTH: 24
<212> TYPE: DNA
<213> ORGANISM: Artificial
<220> FEATURE:
<223> OTHER INFORMATION: Synthesized oligodeoxynucleotide

<400> SEQUENCE: 24
tgttgatact gccggcgggc ggcc                                              24

<210> SEQ ID NO 25
<211> LENGTH: 22
<212> TYPE: DNA
<213> ORGANISM: Artificial
<220> FEATURE:
<223> OTHER INFORMATION: Synthesized oligodeoxynucleotide

<400> SEQUENCE: 25
ataccgctat ccgtcccgcg ac                                                22

<210> SEQ ID NO 26
<211> LENGTH: 24
<212> TYPE: DNA
<213> ORGANISM: Artificial
<220> FEATURE:
<223> OTHER INFORMATION: Synthesized oligodeoxynucleotide

<400> SEQUENCE: 26
tggcgatagg cagggcgctg ggcc                                              24

<210> SEQ ID NO 27
<211> LENGTH: 235
<212> TYPE: PRT
<213> ORGANISM: Bordetella pertussis

<400> SEQUENCE: 27

Asp Asp Pro Pro Ala Thr Val Tyr Arg Tyr Asp Ser Arg Pro Pro Glu
1               5                   10                  15

Asp Val Phe Gln Asn Gly Phe Thr Ala Trp Gly Asn Asn Asp Asn Val
            20                  25                  30

Leu Asp His Leu Thr Gly Arg Ser Cys Gln Val Gly Ser Ser Asn Ser
        35                  40                  45

Ala Phe Val Ser Thr Ser Ser Ser Arg Arg Tyr Thr Glu Val Tyr Leu
    50                  55                  60
```

```
                                 -continued

Glu His Arg Met Gln Glu Ala Val Glu Ala Glu Arg Ala Gly Arg Gly
65              70              75              80

Thr Gly His Phe Ile Gly Tyr Ile Tyr Glu Val Arg Ala Asp Asn Asn
                85              90              95

Phe Tyr Gly Ala Ala Ser Ser Tyr Phe Glu Tyr Val Asp Thr Tyr Gly
            100             105             110

Asp Asn Ala Gly Arg Ile Leu Ala Gly Ala Leu Ala Thr Tyr Gln Ser
            115             120             125

Glu Tyr Leu Ala His Arg Arg Ile Pro Pro Glu Asn Ile Arg Arg Val
        130             135             140

Thr Arg Val Tyr His Asn Gly Ile Thr Gly Glu Thr Thr Thr Thr Glu
145             150             155             160

Tyr Ser Asn Ala Arg Tyr Val Ser Gln Gln Thr Arg Ala Asn Pro Asn
                165             170             175

Pro Tyr Thr Ser Arg Arg Ser Val Ala Ser Ile Val Gly Thr Leu Val
            180             185             190

Arg Met Ala Pro Val Ile Gly Ala Cys Met Ala Arg Gln Ala Glu Ser
            195             200             205

Ser Glu Ala Met Ala Ala Trp Ser Glu Arg Ala Gly Glu Ala Met Val
    210             215             220

Leu Val Tyr Tyr Glu Ser Ile Ala Tyr Ser Phe
225             230             235
```